US011382934B2

(12) United States Patent
Dombkowski et al.

(10) Patent No.: US 11,382,934 B2
(45) Date of Patent: Jul. 12, 2022

(54) METHODS FOR MAKING MIXED ALLERGEN COMPOSITIONS

(71) Applicant: BEFORE BRANDS, Inc., Menlo Park, CA (US)

(72) Inventors: Ashley Dombkowski, Woodside, CA (US); Christopher Cornyn, Woodside, CA (US); Albert E. Rosevear, Jr., Ithaca, NY (US); Olivia M. Weihe, Ithaca, NY (US); Cosmin M. Beliciu, Ithaca, NY (US); Alexandra F. Russell, Ithaca, NY (US); Antoinette de Senna, Livermore, CA (US)

(73) Assignee: BEFORE BRANDS, Inc., Menlo Park, CA (US)

( * ) Notice: Subject to any disclaimer, the term of this patent is extended or adjusted under 35 U.S.C. 154(b) by 0 days.

(21) Appl. No.: 16/630,949

(22) PCT Filed: Jul. 18, 2018

(86) PCT No.: PCT/US2018/042696
§ 371 (c)(1),
(2) Date: Jan. 14, 2020

(87) PCT Pub. No.: WO2019/018529
PCT Pub. Date: Jan. 24, 2019

(65) Prior Publication Data
US 2020/0155615 A1 May 21, 2020

Related U.S. Application Data

(60) Provisional application No. 62/533,826, filed on Jul. 18, 2017, provisional application No. 62/551,395, filed on Aug. 29, 2017.

(51) Int. Cl.

| | |
|---|---|
| *A61K 36/00* | (2006.01) |
| *A61K 35/63* | (2015.01) |
| *A23L 33/19* | (2016.01) |
| *A23L 5/30* | (2016.01) |
| *A23L 29/30* | (2016.01) |
| *A23L 33/105* | (2016.01) |
| *A23L 33/185* | (2016.01) |
| *A23L 33/00* | (2016.01) |
| *A23L 33/155* | (2016.01) |
| *A61K 9/00* | (2006.01) |
| *A61K 31/045* | (2006.01) |
| *A61K 35/57* | (2015.01) |
| *A61K 35/60* | (2006.01) |
| *A61K 36/185* | (2006.01) |
| *A61K 36/22* | (2006.01) |
| *A61K 36/48* | (2006.01) |
| *A61K 36/52* | (2006.01) |
| *A61K 36/736* | (2006.01) |
| *A61K 36/899* | (2006.01) |

(52) U.S. Cl.
CPC ............... *A61K 35/63* (2015.01); *A23L 5/34* (2016.08); *A23L 29/35* (2016.08); *A23L 33/105* (2016.08); *A23L 33/155* (2016.08); *A23L 33/185* (2016.08); *A23L 33/19* (2016.08); *A23L 33/40* (2016.08); *A61K 9/0056* (2013.01); *A61K 31/045* (2013.01); *A61K 35/57* (2013.01); *A61K 35/60* (2013.01); *A61K 36/185* (2013.01); *A61K 36/22* (2013.01); *A61K 36/48* (2013.01); *A61K 36/52* (2013.01); *A61K 36/736* (2013.01); *A61K 36/899* (2013.01); *A23V 2002/00* (2013.01)

(58) Field of Classification Search
CPC ..................................................... A61K 35/60
See application file for complete search history.

(56) References Cited

U.S. PATENT DOCUMENTS

| | | | |
|---|---|---|---|
| 4,031,199 A | 6/1977 | Nieschulz et al. | |
| 5,520,950 A | 5/1996 | Rosenplenter | |
| 6,986,912 B2 | 1/2006 | Kramer | |
| 7,048,928 B2 | 5/2006 | Loria et al. | |
| 7,595,081 B1 | 9/2009 | Bellar | |
| 8,524,242 B2 | 9/2013 | Saito et al. | |
| 8,632,831 B2 * | 1/2014 | Perry | B65D 81/2076 426/107 |
| 8,652,485 B2 | 2/2014 | Hafner et al. | |
| 8,802,056 B2 | 8/2014 | Shea | |
| 9,198,869 B2 | 12/2015 | Walser et al. | |
| 9,271,899 B2 | 3/2016 | Francois | |
| 9,273,129 B2 | 3/2016 | Simon | |
| 9,345,761 B2 | 5/2016 | Esch | |
| 9,402,896 B2 | 8/2016 | Tang | |
| 9,481,716 B2 | 11/2016 | Clark et al. | |
| 9,526,781 B2 | 12/2016 | Koppelman et al. | |

(Continued)

FOREIGN PATENT DOCUMENTS

| | | |
|---|---|---|
| CN | 102048077 A | 5/2011 |
| CN | 102 986 802 A | 3/2013 |

(Continued)

OTHER PUBLICATIONS

American Thoracic Society (2016) "Early introduction of allergenic foods reduces risk of food sensitization," (1 page).
Begin et al. (2014) "Phase 1 results of safety and tolerability in a rush oral immunotherapy protocol to multiple foods using Omalizumab," Allergy Asthma Clin. Immunol., 10(1): 7 (10 pages).
Begin et al. (2014) "Safety and feasibility of oral immunotherapy to multiple allergens for food allergy,"Allergy Asthma Clin. Immunol., 10(1): 1 (8 pages).
Begin et al. (2016) "Erratum to: Safety and feasibility of oral immunotherapy to multiple allergens for food allergy," Allergy Asthma Clin. Immunol., 12: 28 (1 page).

(Continued)

*Primary Examiner* — Qiuwen Mi
(74) *Attorney, Agent, or Firm* — Goodwin Procter LLP

(57) ABSTRACT

Methods of making mixed allergen compositions, e.g., substantially aerobic organism free mixed allergen compositions, and the resulting allergen composition, are provided.

28 Claims, 5 Drawing Sheets

(56) References Cited

U.S. PATENT DOCUMENTS

| | | | |
|---|---|---|---|
| 9,539,318 | B2 | 1/2017 | Dupont et al. |
| 9,731,003 | B2 | 8/2017 | Nadeau |
| 9,744,230 | B2 | 8/2017 | Hearl et al. |
| 9,808,517 | B2 | 11/2017 | Putnam et al. |
| 10,064,936 | B2 | 9/2018 | Nadeau |
| 10,143,742 | B2 | 12/2018 | Nadeau |
| 10,149,904 | B2 | 12/2018 | Nadeau |
| 10,166,286 | B2 | 1/2019 | Nadeau |
| 10,525,124 | B2 | 1/2020 | Nadeau |
| 10,525,125 | B2 | 1/2020 | Nadeau |
| 2004/0000543 | A1* | 1/2004 | Dudek ............... A21B 2/00 219/655 |
| 2005/0025862 | A1* | 2/2005 | Morad ............... A21D 13/30 426/94 |
| 2007/0202211 | A1 | 8/2007 | Altom et al. |
| 2009/0324650 | A1 | 12/2009 | Legon et al. |
| 2010/0041808 | A1* | 2/2010 | Canfer ............... C08K 7/20 524/404 |
| 2010/0278880 | A1 | 11/2010 | Legon et al. |
| 2011/0229523 | A1 | 9/2011 | Koppelman et al. |
| 2012/0207815 | A1 | 8/2012 | Benhamou et al. |
| 2013/0108706 | A1 | 5/2013 | Svennevig |
| 2013/0218132 | A1 | 8/2013 | Francois |
| 2013/0302374 | A1 | 11/2013 | Esch |
| 2014/0010845 | A1 | 1/2014 | Brimnes et al. |
| 2014/0027445 | A1 | 1/2014 | Scheurs et al. |
| 2014/0271721 | A1 | 9/2014 | Walser et al. |
| 2015/0050301 | A1 | 2/2015 | Kettner et al. |
| 2015/0150956 | A1 | 6/2015 | Henot et al. |
| 2015/0343075 | A1 | 12/2015 | Raff |
| 2016/0030553 | A1 | 2/2016 | Legon |
| 2016/0051593 | A1 | 2/2016 | Raff |
| 2016/0051639 | A1 | 2/2016 | Raff |
| 2016/0206731 | A1 | 7/2016 | Francois |
| 2016/0228539 | A1 | 8/2016 | Nelson et al. |
| 2016/0235109 | A1 | 8/2016 | Cavestro et al. |
| 2016/0263212 | A1 | 9/2016 | Friedman et al. |
| 2016/0324955 | A1 | 11/2016 | Benhamou et al. |
| 2016/0330998 | A1* | 11/2016 | Jimenez-Marquez ............... A23K 20/189 |
| 2016/0331834 | A1 | 11/2016 | Mondoulet et al. |
| 2017/0056494 | A1 | 3/2017 | Nadeau |
| 2017/0100476 | A1 | 4/2017 | Legon et al. |
| 2017/0112919 | A1 | 4/2017 | Nadeau |
| 2017/0112920 | A1 | 4/2017 | Nadeau |
| 2017/0112921 | A1 | 4/2017 | Nadeau |
| 2017/0151325 | A1 | 6/2017 | Benhamou et al. |
| 2017/0304432 | A1 | 10/2017 | Hearl et al. |
| 2017/0333386 | A1 | 11/2017 | Lila et al. |
| 2017/0360922 | A1 | 12/2017 | Turke |
| 2018/0020712 | A1 | 1/2018 | Brown |
| 2018/0177895 | A1 | 6/2018 | Mills et al. |
| 2018/0200361 | A1 | 7/2018 | Simon et al. |
| 2019/0038741 | A1 | 2/2019 | Nadeau |
| 2019/0060444 | A1 | 2/2019 | Nadeau |
| 2019/0060445 | A1 | 2/2019 | Nadeau |
| 2019/0269774 | A1 | 9/2019 | Dombkowski et al. |
| 2019/0365885 | A1 | 12/2019 | Nadeau |
| 2019/0381168 | A1 | 12/2019 | Nadeau |
| 2020/0171145 | A1 | 6/2020 | Nadeau |

FOREIGN PATENT DOCUMENTS

| | | |
|---|---|---|
| CN | 104273238 A | 1/2015 |
| EP | 155760 A * | 9/1985 |
| WO | WO-2001040264 | 6/2001 |
| WO | WO-2013078510 A1 | 6/2013 |
| WO | WO-2015042402 A1 | 3/2015 |
| WO | WO-2015185684 A1 | 12/2015 |
| WO | WO-2016020336 A1 | 2/2016 |
| WO | WO-2016134291 A2 | 8/2016 |
| WO | WO-2017048860 A1 | 3/2017 |
| WO | WO-2017139558 A1 | 8/2017 |
| WO | WO-2018065538 A1 | 4/2018 |
| WO | WO-2018093932 A2 | 5/2018 |
| WO | WO-2018094390 A1 | 5/2018 |
| WO | WO-2018112553 A1 | 6/2018 |
| WO | WO-2020113060 A1 | 6/2020 |

OTHER PUBLICATIONS

Bunyavanich et al. (2014) "Peanut, milk, and wheat intake during pregnancy is associated with reduced allergy and asthma in children," J. Allergy Clin. Immunol., 133(5): 1373-82.

Chinthrajah et al. (2016) "Molecular and cellular mechanisms of food allergy and food tolerance," J. Allergy Clin. Immunol., 137(4):984-97.

Choi et al. (2007) "Consumer-Based Optimization of a Third-Generation Product Made from Peanut and Rice Flour," Journal of Food Science, 72(7): S443-S449.

Cuello-Garcia et al. (2015) "Probiotics for the prevention of allergy: A systematic review and meta-analysis of randomized controlled trials," J. Allergy Clin. Immunol., 136(4):952-61.

Du Toit et al. (2008) "Early consumption of peanuts in infancy is associated with a low prevalence of peanut allergy," J. Allergy Clin. Immunol., 122(5): 984-991.

Du Toit et al. (2015) "Randomized Trial of Peanut Consumption in Infants at Risk for Peanut Allergy," N. Engl. J. Med., 372(9):803-13.

Du Toit et al. (2016) "Effect of Avoidance on Peanut Allergy after Early Peanut Consumption," N. Engl. J. Med., 374(15):1435-43.

Du Toit et al. (2016) "Prevention of food allergy," J. Allergy Clin. Immunol., 137(4):998-1010.

Dyer et al. (2015) "Epidemiology of childhood peanut allergy," Allergy Asthma Proc., 36(1):58-64.

Extended European Search Report for European Application No. 16753171.4, dated Jun. 11, 2018 (8 pages).

Favorite Brand Name Recipe Cookbook. Beekman House, New York 1991, pp. 290 and 296 (Cherry Winks and Shredded Wheat Cookies).

Feeney et al. (2016) "Impact of peanut consumption in the LEAP Study: Feasibility, growth, and nutrition," J. Allergy Clin. Immunol., 138(4):1108-1118.

Frazier et al. (2013) "Prospective Study of Peripregnancy Consumption of Peanuts or Tree Nuts by Mothers and the Risk of Peanut or Tree Nut Allergy in Their Offspring," JAMA Pediatr., 168(2):156-162.

Gupta et al. (2011) "The prevalence, severity, and distribution of childhood food allergy in the United States," Pediatrics. 128(1):e9-17.

Gupta et al. (2013) "Factors associated with reported food allergy tolerance among US children," Ann. Allergy Asthma Immunol., 111(3):194-198.

Gupta et al. (2013) "The economic impact of childhood food allergy in the United States," JAMA Pediatr., 167(11):1026-31.

Howard et al. (2010) "Analysis of Ingredient Functionality and Formulation Optimization of an Instant Peanut Beverage Mix," Journal of Food Science, 75(1): S8-S19.

Howard et al. (2011) "Analysis of Ingredient Functionality and Formulation Optimization of Pasta Supplemented with Peanut Flour" Journal of Food Science, 76(1): E40-E47.

International Search Report for PCT/US2016/018731, dated Aug. 22, 2016 (5 pages).

International Search Report for PCT/US2018/042696, dated Sep. 24, 2018 (5 pages).

Kando et al. (2011) "Oral Immunotherapy to the Food-allergic children," Bulletin of Japanese Pediatrics, No. 41, éÉ.91-94.

Katz et al. (2010) "Early exposure to cow's milk protein is protective against IgE-mediated cow's milk protein allergy," J. Allergy Clin. Immunol., 126(1):77-82.

Kim et al. (2016) "Dietary antigens limit mucosal immunity by inducing regulatory T cells in the small intestine," Science, 351(6275):858-63.

Koplin et al. (2010) "Can early introduction of egg prevent egg allergy in infants? A population-based study," J. Allergy Clin. Immunol., 126(4):807-13.

(56) References Cited

OTHER PUBLICATIONS

Koplin et al. (2016) "Understanding the feasibility and implications of implementing early peanut introduction for prevention of peanut allergy," J. Allergy Clin. Immunol., 138(4):1131-1141.
Kristensen et al. (2016) "Alterations in fecal microbiota composition by probiotic supplementation in healthy adults: a systematic review of randomized controlled trials," Genome Med., 8(1):52.
Kristiansen et al. "Allergen immunotherapy for the prevention of allergy: A systematic review and meta-analysis." Pediatr Allergy Immunol. Feb. 2017;28(1 ): 18-29. doi: 10.1111/pai .12661. Epub Dec. 12, 2016.
Kull et al. (2006) "Fish consumption during the first year of life and development of allergic diseases during childhood," Allergy, 61: 1009-1015.
Lau et al. (2012) "Parent report of childhood shellfish allergy in the United States," Allergy Asthma Proc., 33(6):474-80.
Martignago et al. "Preventive actions of allergen immunotherapy: the facts and the effects in search of evidence." Clin Mol. Allergy 2017; 15: 13. Published online Jun. 15, 2017. doi: 10.1186/s12948-017-0070-7.
Mosha et al. (2004) "Nutritional value and acceptability of homemade maize/sorghum-based weaning mixtures supplemented with rojo bean flour, ground sardines and peanut paste," International Journal of Food Sciences and Nutrition, 55(4): 301-315.
Nwaru et al. (2010) "Age at the Introduction of Solid Foods During the First Year and Allergic Sensitization at Age 5 Years," Pediatrics, 125(1):50-9.
Nwaru et al. (2013) "Timing of infant feeding in relation to childhood asthma and allergic diseases," J. Allergy Clin. Immunol., 131(1): 78-86.
Otani et al. (2014) "Multiple-allergen oral immunotherapy improves quality of life in caregivers of food-allergic pediatric subjects," Allergy Asthma Clin. Immunol., 10(1):25 (7 pages).
Ozdemir (2010) "Various effects of different probiotic strains in allergic disorders: an update from laboratory and clinical data," Clin. Exp. Immunol., 160(3):295-304.
Perkin et al. (2016) "Randomized Trial of Introduction of Allergenic Foods in Breast-Fed Infants," N. Engl. J. Med., 374(18):1733-43.
Prinyawiwatkul et al. (1993) "Optimization of Sensory Qualities of an Extruded Snack Based on Cornstarch and Peanut Flour," Lebensm.-Wiss. u.-Technol. (26(5): 393-399.
Reilly et al. (2016) "The Gluten-Free Diet: Recognizing Fact, Fiction, and Fad," J. Pediatr., 175:206-10.
Reisacher, et al. (2016) "Oral mucosal immunotherapy for allergic rhinitis: A pilot study," Allergy Rhinol., 7(1):21-8.
Rudders et al. (2015) "Sunlight, vitamin D and food allergy," Curr. Opin. Allergy Clin. Immunol., 15(4):350-7.
Ryan et al. (2016) "Successful immunotherapy induces previously unidentified allergen-specific CD4+ T-cell subsets," Proc. Natl. Acad. Sci. U.S.A., 113(9):E1286-95.
Shaikh et al. (1993) "A retrospective study on the safety of immunotherapy in pregnancy," Clin. Exp. Allerg. 23(10): 857-860.
Shredded wheat nutritional information, 2017.
Syed et al. (2014) "Peanut oral immunotherapy results in increased antigen-induced regulatory T-cell function and hypomethylation of forkhead box protein 3 (FOXP3)," J. Allergy Clin. Immunol., 133(2):500-10.
Takagi et al. (2005) "A rice-based edible vaccine expressing multiple T cell epitopes including oral tolerance for inhibition of Th2-mediated IgE responses," PNAS, 102(48): 17525-17530.
The Journal of Pediatrics (2016) "The Gluten-Free Diet in Children: Do the Risks Outweigh the Benefits?" (2 pages).
Tran et al. (2016) "The Effects of Infant Feeding Practices on Food Sensitization in a Canadian Birth Cohort," American Thoracic Society 2016 International Conference, Session: D31 Novel Mechanisms of Allergy and Airway Inflammation, Abstract 8568 (2 pages).
Warren et al. (2013) "The epidemiology of milk allergy in US children," Ann. Allergy Asthma Immunol., 110(5):370-4.
Weinstock (2016) "A Glimpse of Microbial Power in Preventive Medicine," JAMA Pediatr. 170(1):11.
Written Opinion for PCT/US2016/018731, dated Aug. 2, 2016 (6 pages).
Written Opinion for PCT/US2018/042696, dated Sep. 24, 2018 (12 pages).
Zolkipli et al. (2015) "Randomized controlled trial of primary prevention of atopy using house dust mite allergen oral immunotherapy in early childhood," J. Allergy Clin. Immunol., 136(6):1541-7.

\* cited by examiner

METHODS FOR MAKING MIXED ALLERGEN COMPOSITIONS

CROSS-REFERENCE TO RELATED APPLICATIONS

This application is a § 371 National Stage of International (PCT) Application No. PCT/US2018/042696, filed Jul. 18, 2018, which claims the benefit of and priority to U.S. Provisional Patent Application No. 62/533,826, filed Jul. 18, 2017, and U.S. Provisional Patent Application No. 62/551,395, filed Aug. 29, 2017. The entire disclosures of each of these applications are hereby incorporated by reference herein for all purposes.

BACKGROUND

Allergy is a disorder of the immune system characterized by the occurrence of allergic reactions to normally harmless environmental substances. Allergies are caused by allergens, which may be present in a wide variety of sources, including but not limited to pollens or other plant components, dust, molds or fungi, foods, additives, latex, transfusion reactions, animal or bird danders, insect venoms, radiocontrast medium, medications or chemicals. Common allergic reactions include eczema, hives, hay fever, asthma, and reactions to venoms. Mild allergies like hay fever are highly prevalent in the human population and cause symptoms such as allergic conjunctivitis, itchiness, and runny nose. In some people, severe allergies to environmental or dietary allergens or to medication may result in life-threatening anaphylactic reactions and potentially death, if left untreated.

A food allergy is an adverse immune response to a food allergen, e.g., a food protein. Common food allergens are found in shellfish, peanuts, tree nuts, fish, milk, eggs, soy and fresh fruits such as strawberries, mangoes, bananas, and apples. Immunoglobulin E (IgE)-mediated food allergies are classified as type-I immediate hypersensitivity reactions. These allergic reactions have an acute onset (from seconds to one hour) and the accompanying symptoms may include angioedema (soft tissue swelling of the eyelids, face, lips, tongue, larynx and trachea), hives, itching of the mouth, throat, eyes, or skin, gastrointestinal symptoms such as nausea, vomiting, diarrhea, stomach cramps, or abdominal pain, rhinorrhea or nasal congestion, wheezing, shortness of breath, or difficulty swallowing, and even anaphylaxis, a severe, whole-body allergic reaction that can result in death. It is estimated that 1 out of 12 children under 21 years of age have a doctor's diagnosis of food allergies, and over $24 billion is spent per year on health care costs for food allergic reactions, largely due to about 90,000 visits to the ER per year in the U.S. due to food induced anaphylactic symptoms. Moreover, there are still deaths that occur every year due to fatal food allergies.

Accordingly, there exists a need in the art for allergen compositions that can prevent and/or treat allergies, and methods for making allergen compositions to prevent and/or treat allergies

SUMMARY

The disclosure is directed, at least in part, to a method for producing a substantially aerobic organism free mixed allergen composition. For example, this disclosure provides a method for producing a substantially aerobic organism free mixed allergen composition comprising: providing a mixed allergen composition comprising 6 or more allergens, e.g., 6 to 20 allergens, and a bulking agent, wherein the mixed allergen composition comprises at least 6% fat content; milling the mixed allergen composition in a conical mill to obtain a milled composition with substantially consistent particle size; and applying microwaves or radio frequency interference to the milled composition so that the milled composition is heated to at least 190° F. for at least 30 minutes, thereby to obtain the substantially aerobic organism free mixed allergen composition. In certain embodiments, the mixed allergen composition comprises at least 12% fat content.

As part of a contemplated method, milling the mixed allergen composition may comprise using a rotor speed of about 9000 RPM and/or passing the mixed allergen composition through a screen with an opening size of about 0.033 inches. As part of a contemplated method, milling the mixed allergen composition may comprise applying a vacuum suction through the conical mill.

A contemplated method may further comprise wetting the milled composition, e.g., to a moisture content of about 6% to about 9%, e.g., about 9%, and/or a water activity of about 0.65 to about 0.8, e.g. about 0.75 to about 0.8, prior to applying microwaves or radio frequency interference to the milled mixed allergen composition. A contemplated method may further comprise pressurizing the milled composition, e.g., to at least 30 psi for at least 30 minutes. In certain embodiments, applying microwaves or radio frequency interference to the milled composition and pressurizing the milled composition are conducted simultaneously.

As part of a contemplated method, the milled composition may be heated to at least 200° F. for at least 60 minutes, e.g., to at least 230° F. for at least 60 minutes. As part of a contemplated method, the milled composition may be heated to no more than 250° F. and/or for no more than 2, 5, 10, 30, 60, 120 or 1000 minutes. As part of a contemplated method, the milled composition may be heated in a microwave blender, e.g., a microwave blender that includes a 75,000 watt microwave transmitter.

In certain embodiments, a contemplated substantially aerobic organism free mixed allergen composition has fewer than about 4.5, about 4, about 3.5, about 3, about 2.5, about 2, or about 1.5 log CFU/g total aerobic organisms, and/or the substantially aerobic organism free mixed allergen composition has fewer than about 1 log CFU/g total coliforms.

In certain embodiments, the substantially aerobic organism free mixed allergen composition has at least about 0.5, about 1, about 1.5, about 2, about 2.5, about 3, about 3.5, or about 4 log CFU/g fewer aerobic organisms than the mixed allergen composition. In certain embodiments, the substantially aerobic organism free mixed allergen composition has a substantially similar protein structure as the mixed allergen composition, as measured by SDS-PAGE and/or a substantially similar allergen effect as the mixed allergen composition, as measured by immune response in a patient.

It is contemplated that the bulking agent may comprise a sugar. It is contemplated that the mixed allergen composition may, e.g., comprise equal parts by protein mass of: at least one nut flour, wherein each nut flour is selected from the group consisting of peanut flour, almond flour, walnut flour, cashew flour, hazelnut flour, pecan flour and pistachio flour; at least one fish powder, wherein each fish powder is selected from the group consisting of cod powder and salmon powder; wheat; and powdered hen's egg or egg white. In certain embodiments, the mixed allergen composition may further comprise at least one additional allergen component, e.g., soy and/or an additional allergen component selected from oat flour, sesame seed flour, and shrimp flour. In certain embodiments, the mixed allergen composition may further comprise vitamin D. In an exemplary embodiment, the mixed allergen composition comprises 30 mg by protein weight shrimp powder; 30 mg by protein weight almond powder; 30 mg by protein weight wheat; 30 mg by protein weight cod powder; 30 mg by protein weight powdered hen's egg; and 400 IU vitamin D.

Also contemplated herein is a substantially aerobic organism free mixed allergen composition produced by a disclosed method, and a food product comprising a substantially aerobic organism free mixed allergen composition produced by a disclosed method.

DETAILED DESCRIPTION

Figure 1:
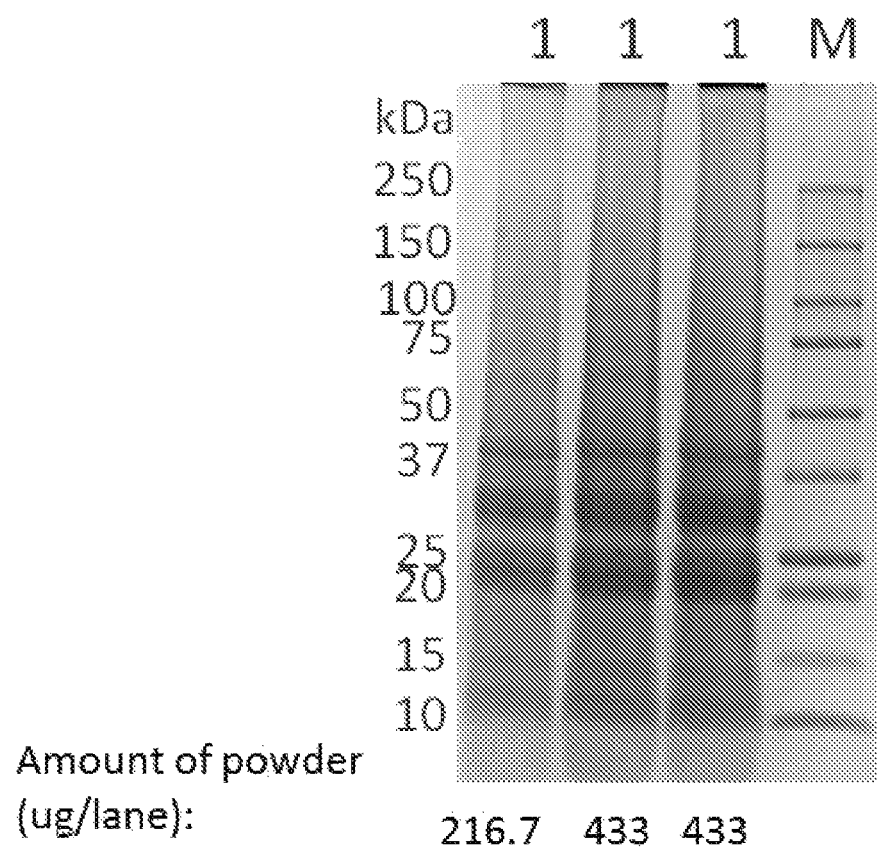
FIG. 1 is an SDS-PAGE gel showing a mixed allergen composition (Product A) following treatment in a WaveMix microwave blender.

Disclosed herein are methods for making a mixed allergen composition, e.g., a substantially aerobic organism free mixed allergen composition. A disclosed process may, e.g., comprise one or more of the following steps: providing a mixed allergen composition comprising 6 or more allergens, e.g., 6 to 20 allergens, and a bulking agent, wherein the mixed allergen composition comprises at least 6% fat content; milling the mixed allergen composition in a conical mill to obtain a milled composition with substantially consistent particle size; and applying microwaves or radio frequency interference to a mixed allergen composition, e.g., a milled mixed allergen composition, so that the composition is heated to at least 190° F. for at least 30 minutes. In certain embodiments, the mixed allergen composition comprises at least 12% fat content.

The mixed allergen composition may include any allergen or allergen composition described herein. In certain embodiments, a mixture of allergens may comprise one, two, or more allergens each independently selected from the allergens disclosed in the Examples herein. For example, in certain embodiments, a composition may comprise one, two, or more allergens selected from a group consisting of peanut, soy, almond, cashew, hazelnut, pecan, pistachio, walnut, wheat, oat, milk, egg, cod, salmon, shrimp, and sesame. In certain embodiments, the dry mixture of allergens includes about 30 mg each of peanut, soy, almond, cashew, hazelnut, pecan, pistachio, walnut, wheat, oat, milk, egg, cod, salmon, shrimp, and sesame. It will be appreciated that the allergens contemplated herein may each be present as a meal, flour, powder, and/or protein concentrate.

Contemplated bulking agents may include any bulking agent described herein. In certain embodiments, the bulking agent comprises a sugar, e.g., sucrose, maltodextrin, or a combination thereof. Without wishing to be bound by theory, it is believed that bulking agents reduce the fat content of an allergen mixture to aid in downstream processing, e.g., milling.

In certain embodiments, a disclosed method comprises milling the mixed allergen composition, e.g., in a conical mill. The milling may, e.g., comprise using a rotor speed of about 9000 RPM, or may, e.g., further comprise applying a vacuum suction through the conical mill. The milling may, e.g., comprise passing the mixed allergen composition through a screen with an opening size of about 0.033 inches. Without wishing to be bound by theory, it is believed that milling reduces grittiness and large particle size and increases blend homogeneity.

In certain embodiments, a disclosed method comprises applying microwaves or radio frequency interference to a mixed allergen composition, e.g., a milled mixed allergen composition, so that the composition is heated to at least 190° F. for at least 30 minutes, e.g., at least 200° F. for at least 60 minutes, or at least 230° F. for at least 60 minutes. In certain embodiments, a mixed allergen composition, e.g., a milled mixed allergen composition, may be heated to no more than 250° F. and/or for no more than 360 or 1000 minutes. In certain embodiments, the composition is heated in a microwave blender, e.g., a microwave blender that includes a 75,000 watt microwave transmitter. In certain embodiments, a disclosed method comprises applying pressure to a mixed allergen composition, e.g., a milled mixed allergen composition, e.g., to at least 30 psi for at least 30 minutes. In certain embodiments, applying microwaves or radio frequency interference to the composition and pressurizing the composition are conducted simultaneously.

In certain embodiments, a disclosed method comprises wetting a mixed allergen composition, e.g., a milled mixed allergen composition. The composition may, e.g., be wetted prior to applying microwaves or radio frequency interference to heat the composition. In certain embodiments, the composition is wetted to a moisture content of about 6% to about 9%, e.g., 9%, and/or a water activity of about 0.65 to about 0.8, e.g., about 0.75 to about 0.8.

In certain embodiments, a substantially aerobic organism free mixed allergen composition has fewer than about 4.5, about 4, about 3.5, about 3, about 2.5, about 2, or about 1.5 log CFU/g total aerobic organisms. In certain embodiments, a substantially aerobic organism free mixed allergen composition has fewer than about 1 log CFU/g total coliforms.

It is contemplated that, in certain embodiments, a substantially aerobic organism free mixed allergen composition has fewer aerobic organisms than a mixed allergen composition that has not been prepared by a disclosed process, e.g., a mixed allergen composition that has not been heated by microwaves or radio frequency interference, e.g., to at least 190° F. for at least 30 minutes, at least 200° F. for at least 60 minutes, or at least 230° F. for at least 60 minutes. For example, in certain embodiments, the substantially aerobic organism free mixed allergen composition has at least about 0.5, about 1, about 1.5, about 2, about 2.5, about 3, about 3.5, or about 4 log CFU/g fewer total aerobic organisms than a mixed allergen composition that has not been prepared by a disclosed process, e.g., a mixed allergen composition that has not been heated by microwaves or radio frequency interference, e.g., to at least 190° F. for at least 30 minutes, at least 200° F. for at least 60 minutes, or at least 230° F. for at least 60 minutes.

It is contemplated that, in certain embodiments, a disclosed method does not substantially affect the structure and/or function of the mixed allergen composition. For example, in certain embodiments, a substantially aerobic organism free mixed allergen composition has a substantially similar protein structure, as measured by SDS-PAGE, as a mixed allergen composition that has not been prepared by a disclosed process, e.g., a mixed allergen composition that has not been heated by microwaves or radio frequency interference, e.g., to at least 190° F. for at least 30 minutes or at least 230° F. for at least 60 minutes. Similarly, in certain embodiments, a substantially aerobic organism free mixed allergen composition has a substantially similar allergen effect, as measured by immune response in a patient, as a mixed allergen composition that has not been prepared by a disclosed process, e.g., a mixed allergen composition that has not been heated by microwaves or radio frequency interference, e.g., to at least 190° F. for at least 30 minutes or at least 230° F. for at least 60 minutes.

As used herein, an "allergenic composition" is understood to mean a composition that includes one or more different allergens or allergenic components. Allergenic compositions are understood to include "mixed allergen compositions" that include two or more different allergens, where any two given allergens are different if they are distinct from each other, e.g., they are compounds described by different chemical formula or compositions described by different components and/or amounts thereof. The number of different allergens in a composition may vary, as desired. In certain embodiments, a mixed allergen composition comprises 2 or more different allergens, such as 3 or more different allergens, 4 or more different allergens, 5 or more different allergens, 6 or more different allergens, 7 or more different allergens, 8 or more different allergens, 9 or more different allergens, 10 or more different allergens, 15 or more different allergens, 20 or more different allergens, 25 or more different allergens, 30 or more different allergens, 40 or more different allergens, 50 or more different allergens, 75 or more different allergens, or 100 or more different allergens. In certain embodiments, a mixed allergen composition comprises 100 or fewer different allergens, such as 75 or fewer different allergens, 50 or fewer different allergens, 25 or fewer different allergens, 15 or fewer different allergens, or 10 or fewer different allergens. In certain embodiments, a composition may include 2 to 20 different allergens, 2 to 100 different allergens, or 2 to 1000 different allergens. In further embodiments, a composition may comprise 6 to 20 different allergens. In certain embodiments, a composition may consist essentially of 6 to 20 different protein allergens.

Allergens present in an allergenic composition may vary, where in some instances an allergen present in the composition is one that induces an allergy in a susceptible subject. Allergens include any antigen, or active derivative thereof, that elicits a specific IgE response. Antigens include any substance that can stimulate the production of antibodies and can combine specifically with them. Allergens may have little or no intrinsic toxicity by themselves, but cause a pathological condition due to their ability to elicit an IgE-associated immune response, and, upon subsequent exposure, due to their ability to elicit IgE- and/or T cell-dependent hypersensitivity reactions. As such, an allergen includes any substance which is capable of stimulating a typical hypersensitivity reaction in atopic subjects. Allergens that may be present in a given allergenic composition include any substance found in a variety of different sources, e.g., foods, drugs, perfume, plants, the environment or biological systems (e.g., prokaryotic or eukaryotic cells or viruses), as well as chemical allergens.

It is appreciated that reference to an allergen or an allergenic composition may each include a plurality of different proteins as found in the naturally occurring allergen (either raw or cooked). For example, a provided food product may include a peanut allergen composition (which would include substantially all peanut proteins present in e.g., defatted peanuts, ground peanuts, etc.). As used herein the phrase "complete allergen" refers to all possible antigenic components of a given food product.

Allergens of interest include nut allergens. Nut allergens are allergens that include one or more compounds found in nuts, e.g., dry fruits that include an edible kernel or meat enclosed in a woody or leathery shell. Nut allergens of interest include, e.g. peanut allergens, (e.g., rAra h 1, rAra h 2, rAra h 3, rAra h 8 PR-10, rAra h 9 LTP, or peanut complete allergen), brazil nut allergens (e.g., rBer e 1, or brazil nut complete allergen), hazelnut or filbert allergens (e.g., rCor a 1 PR-10, rCor a 8 LTP, nCor a 9, rCor a 14, or hazel nut complete allergen), walnut allergens (e.g., rJug r 1, rJug r 3 LTP, or walnut complete allergen), cashew allergens (e.g., cashew component allergens, or cashew complete allergen), pistachio allergens (e.g., pistachio component allergens, or pistachio complete allergen), pecan allergens (e.g., pecan component allergens, or pecan complete allergen), almond allergens (e.g., almond component allergens, or almond complete allergen), or tree nut component package allergens (e.g., one or more allergens from e.g., cashew nut, walnut, hazelnut, or brazil nut).

Allergens of interest include animal allergens. Animal allergens are allergens that include one or more compounds found in animals, including both vertebrates and invertebrates. Vertebrate animal allergens that may be present in an allergenic composition include avian allergens (e.g., egg allergens, e.g., nGal d 1 Ovomucoid, n Gal d 2 Ovalbumin, nGal d 3 Conalbumin, or egg white complete allergen), mammalian allergens (e.g. milk allergens, e.g., nBos d 4 alpha-lactalbumin, nBos d 5 beta-lactoglobulin, nBos d 8 Casein, nBos d Lactoferrin, or milk complete allergen), or fish allergens (e.g., rCyp c 1, rGad c 1, cod complete allergen, white fish allergens, or pink fish allergens). Invertebrate animal allergens that may be present in an allergenic composition include crustacean allergens (e.g., shrimp allergens, e.g., rPen a 1 tropomyosin, or shrimp complete allergen), or insect allergens (e.g., bee sting venom allergen, wasp sting venom allergen, or mosquito bite allergen).

Allergens of interest include non-nut plant allergens, i.e., plant allergens that are not nut allergens. Plant allergens are allergens that include one or more compounds found in plants. Plant allergens of interest include wheat allergens (e.g., rTri a 19 Omega-5 Gliadin, gliadin wheat, rTri a 14 LTP, or wheat complete allergen), fruit allergens (e.g., kiwi allergens, e.g., rAct d 8 PR-10, or kiwi complete allergen), vegetable allergens (e.g., carrot allergens, or celery allergens, e.g., rApi g 1.01 PR-10, rPhl p 12, or celery complete allergen), CCD MUXF3 from Bromelain, legume allergens (e.g., soy allergens or chickpea allergens, e.g., rGly m 4 PR-10, nGly m 5 Beta-conglycinin, nGly m 6 Glycinin, or soy complete allergen), stone fruit allergens, e.g., f419, f420, f421, f95, f242, o214 rPru p 1 PR-10, rPru p 3 LTP, or stone fruit primary complete allergen), oat allergens (e.g., oat component allergens, or oat complete allergen), or seed allergens (e.g., sesame allergens, e.g., sesame seed component allergens, or sesame seed complete allergen).

Additional types of allergens that may be present in an allergenic unit, component or composition include, e.g., non-food animal allergens (e.g., cats or dog fur and dander, cockroach calyx, dust mite excretion), drug allergens (penicillin, sulfonamides, salicylates, local anesthetics), mold spore allergens, latex allergens, metal allergens, or plant pollen allergens (e.g. from grass, e.g., ryegrass or timothy-grass, from weeds, e.g., ragweed, plantago, nettle, Artemisia, vulgaris, Chenopodium album, sorrel, or e.g., from trees, e.g., birch alder, hazel, hornbeam, aesculus, willow, poplar, platanus, tilia, or olea).

In certain embodiments, an allergenic composition may comprise one, two, or more allergens selected from a group consisting of cashew, pistachio, walnut, pecan, white fish, pink fish, shrimp, peanut, soy, hazelnut, almond, milk, egg, crab, wheat, and sesame.

In certain embodiments, an allergenic composition may comprise one, two, or more allergens selected from a group consisting of peanut, soy, almond, cashew, hazelnut, pecan, pistachio, walnut, wheat, oat, milk, egg, cod, salmon, shrimp, and sesame.

The amount of a given allergen in an allergenic composition, as desired. In certain embodiments, the amount of a given allergen ranges from about 1 to about 15,000 mg, about 5 to about 15,000 mg, about 10 to about 10,000 mg, about 15 to about 5,000 mg, about 10 to about 100 mg, or about 15 to about 100 mg. In certain embodiments, the amount of a given allergen is about 30 mg. The weight percentage of a given allergen in an allergenic unit, component, or may vary, as desired. In certain embodiments, the weight percentage of a given allergen in an allergenic unit, component, or composition ranges from about 0.1 to about 99.9 wt. %, about 0.1 to about 15 wt. %, about 15 to about 99.9 wt. %, or about 25 to about 65 wt. %. The amount of a given allergen in an allergenic unit, component, or composition may be recited by total mass, or by protein mass, which may vary for a given allergen depending upon the weight percentage of protein in that allergen.

In certain embodiments, if more than one allergen is present in an allergenic composition, e.g., in a mixed allergen composition, any two of the mixed allergens, or all of the mixed allergens, are present in equal parts, e.g., in a 1:1 ratio, such that each allergen is present in the composition in equal weight.

A disclosed allergenic composition may include one or more vitamins, as desired. Vitamins that may be present include. e.g., vitamin A (e.g., in an amount ranging from 1 to 35,000 IU), vitamin C (e.g., in an amount ranging from about 1 to about 1,000 mg), vitamin D (e.g., in an amount ranging from about 1 to about 4,000 IU, i.e., from about 0.025 to about 100 mcg), vitamin E (e.g., in an amount ranging from about 1 to about 450 IU), vitamin K (e.g., in an amount ranging from about 1 to about 250 mcg), vitamin B-1 (thiamin; e.g., in amount ranging from about 1 to about 15 mg), vitamin B-2 (riboflavin; e.g., in an amount ranging from about 1 to about 17 mg), vitamin B-3 (niacin; e.g., in an amount ranging from about 1 to about 200 mg), vitamin B-5 (pantothenic acid; e.g., in an amount ranging from about 1 to about 100 mg), vitamin B-6 (pyridoxine; e.g., in an amount ranging from about 1 to about 30 mg), vitamin B-9 (folic acid; e.g., in an amount ranging from about 1 to about 4,000 mcg), vitamin B-12 (cobalamin; e.g., in an amount ranging from about 1 to about 250 mcg), vitamin H (biotin; e.g., in an amount ranging from about 1 to about 1,000 mcg) and combinations thereof. In certain embodiments, an allergenic unit, component, or composition comprises vitamin D. In certain embodiments, an allergenic unit, component, or composition comprises about 400 IU, i.e., about 10 mcg, of vitamin D.

It is appreciated that a disclosed allergen or protein may be in the form of a flour, powder, meal, paste, etc. In some embodiments, a disclosed unit or composition comprises about 30 mg protein by weight of each specific protein or allergen contained therein, e.g. about 30 mg by protein weight of an allergenic component each selected as described herein from peanut, tree nut, cow's milk, soy, egg, fish and shellfish.

Also provided are physiological acceptable compositions that include a disclosed allergenic composition and a physiologically acceptable delivery vehicle. Disclosed allergenic units, components, or compositions can be incorporated into a variety of formulations for administration to a subject. More particularly, a disclosed allergenic unit, component, or composition can be formulated into a physiological acceptable composition by combination with appropriate, physiologically acceptable carriers or diluents, for example, a vegetable oil. In certain embodiments, a disclosed allergenic unit, component, or composition is designed for oral administration, for example, as foods, tablets, troches, lozenges, aqueous or oily suspensions, dispersible powders or granules, emulsions, hard or soft capsules, or syrups or elixirs, gums, etc. Compositions intended for oral use may be prepared according to any convenient protocol for the manufacture of pharmaceutical compositions and such compositions may contain one or more agents selected from the group consisting of sweetening agents, flavoring agents, coloring agents and preserving agents in order to provide palatable preparations.

Also provided are allergenic compositions that are food products. Food products of interest include a disclosed allergenic unit, component, or composition in combination with a food delivery vehicle. By food delivery vehicle is meant a delivery vehicle that is a nourishing substance that is eaten, drunk, or otherwise taken into the body to sustain life, provide energy, promote growth, etc. Examples of food delivery vehicles or food products of interest include, but are not limited to: baby or infant formula, baby food (e.g., pureed food suitable for infant or toddler consumption), chips, cookies, breads, spreads, creams, yogurts, liquid drinks, chocolate containing products, candies, ice creams, cereals, coffees, pureed food products, etc. In certain embodiments, the composition is a food supplement.

In certain embodiments, a disclosed allergenic composition may include a bulking agent. Exemplary bulking agents include maltodextrin, sucrose, trehalose, trehalose dihydrate, mannitol, lactose, dextrose, fructose, raffinose, or any combination thereof. In certain embodiments, the bulking agent comprises maltodextrin, or sucrose, or a combination thereof. In certain embodiments, the bulking agent comprises maltodextrin and sucrose at a weight ratio of about 3:1. In certain embodiments, an allergenic unit, component, or composition may include excipients, e.g., a food safe oil, a polysaccharide (e.g., gellan gum), flavoring, and a food safe salt (e.g., dipotassium phosphate).

In certain embodiments an allergenic composition is an aqueous suspension containing a disclosed allergenic component in admixture with excipients suitable for the manufacture of aqueous suspensions. Such excipients may include suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

In certain embodiments an allergenic composition is an oily suspension containing an allergenic composition suspended in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Disclosed allergenic compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, preservative and flavoring and coloring agents. A disclosed composition may be in the form of a sterile aqueous or oleagenous suspension. This suspension may be formulated according to the known art using those suitable dispersing or wetting agents and suspending agents which have been mentioned above. The sterile preparation may also be a sterile solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Throughout the description, where apparatus, devices, and systems are described as having, including, or comprising specific components, or where processes and methods are described as having, including, or comprising specific steps, it is contemplated that, additionally, there are apparatus, devices, and systems that consist essentially of, or consist of, the recited components, and that there are processes and methods that consist essentially of, or consist of, the recited processing steps.

The foregoing examples are presented herein for illustrative purposes only, and should not be construed as limiting in any way.

EXAMPLES

Example 1

This example describes the selection of ingredients for inclusion an exemplary dry powder mixed allergen composition containing 16 allergenic ingredients (almond, cashew, cod, egg, hazelnut, milk, oat, peanut, pecan, pistachio, salmon, sesame, shrimp, soy, walnut, and wheat)

Ingredients were sourced with primary emphasis on domestic commercial viability, with exceptions made for ingredients that were only available internationally. Successful commercial sourcing of multiple options per each allergenic ingredient led to the development of selection criteria in order to choose the best commercial ingredient to be tested. Attributes screened included maximum protein content and minimum bulking materials, organoleptic attributes, including overall taste, presence of off-notes, grittiness, and ingredient solubility. Ingredients of considerably low protein content, or with large proportions of bulking ingredients, were eliminated from contention. Ingredients were tasted dry to determine the presence of off-flavors, as well as assess the ingredient's grittiness.

The allergenicity of selected ingredients was also confirmed. Two initially selected ingredients, salmon protein and wheat protein, failed protein gels for allergen confirmation. It is hypothesized that since these proteins undergo partial or full hydrolysis in their ingredient processing, the amino acid structure is disrupted such that the polypeptide profile does not result in allergenicity. Despite the processability and organoleptic advantages of these ingredients, salmon powder and wheat gluten powder from different sources replaced the wheat and salmon ingredients in the mixed allergen composition.

Example 2

This example describes the determination of a dry milling process for the preparation of an exemplary dry powder mixed allergen composition containing 16 allergenic ingredients (almond, cashew, cod, egg, hazelnut, milk, oat, peanut, pecan, pistachio, salmon, sesame, shrimp, soy, walnut, and wheat).

A limitation of dry milling is the fat content of the dry blend. Dry blends with fat content above 6% are difficult to mill without considerable processing issues, as the fat seeps from the initial ingredients and obstructs the milling sieve, thus halting the dry milling process altogether. The blend of the 16 allergenic ingredients alone exceeded 38% fat, so a large amount of bulking agent was added in order to feasibly mill the blend.

The 16 protein ingredients were weighed proportionally in order to deliver 30 mg of each protein. Milling of the 16 allergenic ingredient blend with a Quadro Laboratory Scale Dry Mill (FitzMill L1A) at rotor speeds ranging from 5,000 to 9,000 RPM, and screen sizes of 0.020", 0.033", or 0.065", using a blend of sugar and maltodextrin as the bulking agent, allowed for successful milling at a fat content of up to 6%.

Milling variables were explored that allowed for a higher fat content during the milling process to enable a reduced serving size for the dry powder mixed allergen composition. A Quadro L1A SLS Conical Mill was used, which has a higher tip speed and is therefore able to achieve a more efficient milling process. A benchtop vacuum (Craftsman) was attached to the Conical Mill in order to provide suction for the milled powder to pass through the screen, preventing extended residence time on the screen, which could lead to the fat melting and clogging the sieve. Sugar was used as a bulking agent which, unlike maltodextrin, has an abrasive crystalline structure which aids in the milling process. In total, milling of the 16 allergenic ingredient blend with a Quadro L1A SLS Conical Mill at a rotor speed of 9,000 RPM, and screen size of 0.033", using sugar as the bulking agent, and applying vacuum suction, allowed for successful milling at a fat content of up to 12%.

Other milling processes were unable to successfully mill the mixed allergen composition with the desired fat content. Milling the mixed allergen composition with bulking agent at 15% fat content with a Pulvocron and Angled Disintegrator on a 0.5 mm screen resulted in material binding to the screen. Adjusting rotor speed or freezing material in an effort to make it more brittle and resistant to fat melting and smearing had no impact on the process. Milling the mixed allergen composition with bulking agent at 12% fat content in a RMS Roller Grinder resulted in fat melting, sticking to the rolls and blocking the inter-roller gaps. Milling the mixed allergen composition with a Jet Pulverizer at various ratios of protein blend to sugar bulking agent (1:4-1:1.18, corresponding to 6.8%-12% fat content) resulted significant build up in the milling chamber. Lastly, milling the mixed allergen composition with bulking agent at 20% fat content with PowderSize, a jet mill type milling technology, resulting in the blend compacting very quickly in the mill, making milling impossible.

Example 3

This example describes the determination of a sieving process for nut meals or flours in the preparation of an exemplary dry powder mixed allergen composition containing 16 allergenic ingredients (almond, cashew, cod, egg, hazelnut, milk, oat, peanut, pecan, pistachio, salmon, sesame, shrimp, soy, walnut, and wheat).

Four nut flours which contained larger, more visible particles (pecan, pistachio, almond, and cashew) were passed through a #14 and #18 mesh sieve to eliminate the larger particles. Each fraction was tested for protein content using the Dumas method. The results, depicted in TABLE 1, show minimal loss in protein content following each sieving step for each nut tested. The observed protein content after sieving for each nut fell within the acceptable range for the blend, and variation in protein quantity found throughout different mesh sizes is in line with normal agricultural variance from batch to batch. These results demonstrate that sieving through a #14 and/or #18 mesh sieve can be used for any of pecan, pistachio, almond, or cashew flours without impacting protein content.

TABLE 1

| Nut | Sieve Size | Protein (%)* | Percent Change from Unsieved |
|---|---|---|---|
| Pecan | Unsieved | 10.9% | N/A |
| | Above #14 Mesh | 10.6% | −2.75% |
| | Between #14 and #18 Mesh | 10.7% | −1.83% |
| | Below #18 Mesh | 11.4% | +4.59% |
| Pistachio | Unsieved | 21.9% | N/A |
| | Above #14 Mesh | 21.9% | 0.00% |
| | Between #14 and #18 Mesh | 21.9% | 0.00% |
| | Below #18 Mesh | 22.1% | +0.91% |
| Almond | Unsieved | 22.2% | N/A |
| | Above #14 Mesh | 22.2% | 0.00% |
| | Below #18 Mesh | 22.2% | 0.00% |
| Cashew | Unsieved | 17.5% | N/A |
| | Above #14 Mesh | 17.7% | +1.14% |
| | Below #18 Mesh | 17.5% | 0.00% |

Three of the four nuts flours (pecan, pistachio, and almond) showed a significant benefit due to sieving, e.g. with reduced particle size. Accordingly, pecan and almond flour were sieved through the #14 mesh, and pistachio was sieved through the #18 mesh. Using finer sieves was not practical due to the high fat content of the nuts leading to clogging of finer mesh. While sieving did not significantly benefit the cashew flour, it was determined that the cashew flour was fine enough and light-colored enough, and already had a fine particle size distribution, and therefore was suitable to incorporate into the allergen blend without sieving.

Example 4

This example describes the evaluation of the vitamin D content of an exemplary dry powder mixed allergen composition containing 16 allergenic ingredients (almond, cashew, cod, egg, hazelnut, milk, oat, peanut, pecan, pistachio, salmon, sesame, shrimp, soy, walnut, and wheat) throughout various exemplary processing steps to determine the impact of these steps on vitamin D content and blend homogeneity in general.

First, a Ro-Tap test was designed to simulate mechanical stress and extreme vibration that may occur in a stick packaging machine hopper during filling. A batch of exemplary dry mixed allergen composition containing 16 allergenic ingredients was blended with vitamin D, flavor and sugar, mixed, loaded in a cylinder, secured on a Ro-Tap and shaken for 30 minutes. Vitamin D content was tested before the Ro-Tap process, as well as after the Ro-Tap process, from sampling points at the top and the bottom of the cylinder of product. Vitamin D content was assayed by LCMS. The initial vitamin D content in the mixed allergen formulation before the Ro-Tap process was 10.5 mcg/5 g composition. After the Ro-Tap process, a top layer sample contained 9.45 mcg vitamin D/5 g composition, while the bottom layer was tested at 10.3 mcg vitamin D/5 g composition. The results of this experiment suggest that while some vitamin D content differences were measurable in the Ro-Tap product, the extent of any separation is low: in the top layer, vitamin D was depleted by ~10% as a result of the shaking treatment, while the bottom layer did not show any significant increase in vitamin D concentration.

A second experiment was carried out at a pilot plant scale using a placebo formulation containing flax seed meal as a stand-in for a mixed allergen composition, as well as sugar, flavor, and vitamin D. A production and packaging process was carried out. Briefly, the ingredients were pre-blended in a WaveMix microwave blender without microwave heating, the blended ingredients were then heated in the WaveMix microwave blender up to 230° F. for one hour, the product was discharged into poly-lined pails and allowed to cool, and the product was then packaged into individual 5 g stick packs.

Blend homogeneity and vitamin D content were evaluated through the production and packaging process. Due to the flow characteristics of the dry blended formulation, a vibration component was added to the hopper feeding into the stick pack filler, which prompted concerns over vitamin D settling out in the hopper. Stick-pack filling was carried out on two separate dates, and sampling was carried out at the beginning, middle and end of the run each day. For each sampling point, sets of three stick packs were consolidated for sampling, and the tests were performed in triplicate. Results showed an average of 9.78 mcg/5 g at the beginning, 9.32 mcg/5 g in the middle, and 9.57 mcg/5 g at the end for the first day of packaging, and an average of 9.73 mcg/5 g at the beginning, 9.67 mcg/5 g in the middle, and 10.02 mcg/5 g at the end for the second day of packaging. Statistical analysis of data showed no significant or systematic vitamin D settling observed for a placebo formulation production carried out under typical plant operating conditions (vibrating hopper, stick pack filler, etc.). However, as these results consistently showed slightly lower vitamin D content than the target dose of 10 mcg/5 g present in the initial composition, a 20% vitamin D overage was used, where indicated, to ensure that each serving hits the minimum targeted dose of 10 mcg/5 g.

A third experiment was carried out at the pilot plant scale using the mixed allergen composition containing 16 allergenic ingredients, sugar, flavor, flow agent and vitamin D. Briefly, the ingredients were pre-blended in a WaveMix microwave blender without microwave heating, the blended ingredients were then heated in the WaveMix microwave blender up to 230° F. for one hour, the product was discharged into poly-lined pails and allowed to cool, and the product was then packaged into individual 5 g stick packs.

Blend homogeneity and vitamin D content were evaluated through the production and packaging process. Sampling was carried out at the beginning, middle and end of the stick-pack filling run. For each sampling point vitamin D testing was performed in six replicates, in order to increase the power of the statistical analysis. Results showed an average of 10.51 mcg/5 g at the beginning, 11.36 mcg/5 g in the middle, and 11.08 mcg/5 g at the end of the packaging run. Data analysis showed no statistically significant differences in vitamin D concentration throughout a full mixed allergen formulation production carried out under typical plant operating conditions (vibrating hopper, stick pack filler, etc.). These results demonstrate that there is no settling out of vitamin D in the final mixed allergen formulation throughout a full production and packaging process.

In order to further ensure vitamin D homogeneity in a mixed allergen composition, the following process was developed. The 16 allergenic ingredients (almond, cashew, cod, egg, hazelnut, milk, oat, peanut, pecan, pistachio, salmon, sesame, shrimp, soy, walnut, and wheat) were dry blended together, resulting in a high overall fat content blend. Vitamin D was added and dry blended with the 16 allergenic ingredient blend, so that vitamin D ingredient particles can stick to the higher fat, oily nut meal particles, helping to disperse the vitamin D in the finished product matrix. This process further prevents separation or settling of vitamin D in the finished product.

Example 5

The formulation of an exemplary dry powdered mixed allergen composition resulting from the processes described in Examples 1-2 is depicted in TABLE 2. This composition is hereafter referred to as Product A.

TABLE 2

| Ingredient | % Dry Blend |
| --- | --- |
| Peanut Flour | 1.107 |
| Soy Protein Isolate | 0.66 |
| Blanched Almond Flour | 2.64 |
| Cashew Flour | 3.14 |
| Hazelnut Flour | 1.95 |
| Pecan Meal | 6.28 |
| Pistachio Meal | 2.69 |
| Walnut Flour | 1.33 |
| Wheat Gluten Powder | 0.74 |
| Oat Protein Powder | 1.05 |
| Milk Protein Isolate | 0.677 |
| Dried Whole Eggs | 1.15 |
| Codfish Powder | 0.75 |
| Salmon Powder | 1.55 |
| Shrimp Powder | 0.88 |
| Sesame Seed Flour | 0.99 |
| Dry Vitamin D3 100 SD/S | 0.08 |
| Natural Masking Flavor | 9.45 |
| Extra Fine Granulated Sugar | 60.93 |
| Rice concentrate | 2.01 |
| Total | 100 |

The formulation of an additional exemplary dry powdered composition, including brown flax seed, golden flax seed, caramel color, natural masking flavor, sugar (bulking agent), rice concentrate (flow aid ingredient), and vitamin D is depicted in TABLE 3. This composition is hereafter referred to as Product B.

TABLE 3

| Ingredient | % Dry Blend |
| --- | --- |
| Brown Flax Seed | 18.53 |
| Gold Flax Seed | 8.79 |
| Caramel Color | 0.21 |
| Dry Vitamin D3 100 SD/S | 0.08 |
| Natural Masking Flavor | 9.45 |
| Extra Fine Granulated Sugar | 60.93 |
| Rice concentrate | 2.01 |
| Total | 100 |

The formulation of an additional exemplary dry powdered mixed allergen composition resulting from the processes described in Examples 1-2 is depicted in TABLE 4. This composition is hereafter referred to as Product C. Product C was based on the formulation of Product A, and incorporates improvements related to improving the flow of the dry powder product.

TABLE 4

| Ingredient | % Dry Blend |
| --- | --- |
| Peanut Flour | 1.13 |
| Soy Protein Isolate | 0.70 |
| Blanched Almond Flour | 2.80 |
| Cashew Flour | 3.33 |

TABLE 4-continued

| Ingredient | % Dry Blend |
| --- | --- |
| Hazelnut Flour | 2.07 |
| Pecan Meal | 6.67 |
| Pistachio Meal | 2.86 |
| Walnut Flour | 1.41 |
| Wheat Gluten Powder | 0.79 |
| Oat Protein Powder | 1.11 |
| Milk Protein Isolate | 0.71 |
| Dried Whole Eggs | 1.22 |
| Codfish Powder | 0.80 |
| Salmon Powder | 1.65 |
| Shrimp Powder | 0.83 |
| Sesame Seed Flour | 1.05 |
| Dry Vitamin D3 100 SD/S | 0.08 |
| Natural Masking Flavor | 9.40 |
| Extra Fine Granulated Sugar | 59.88 |
| Silicon Dioxide Sipernat 50 | 1.50 |
| Total | 100 |

The formulation of an additional exemplary dry powdered mixed allergen composition resulting from the processes described in Examples 1-2 is depicted in TABLE 5. This composition is hereafter referred to as Product D.

TABLE 5

| Ingredient | % Dry Blend |
| --- | --- |
| Peanut Flour | 1.13 |
| Soy Protein Isolate | 0.70 |
| Blanched Almond Flour | 2.80 |
| Cashew Flour | 3.33 |
| Hazelnut Flour | 2.07 |
| Pecan Meal | 6.67 |
| Pistachio Meal | 2.86 |
| Walnut Flour | 1.41 |
| Wheat Gluten Powder | 0.79 |
| Oat Protein Powder | 1.11 |
| Milk Protein Isolate | 0.71 |
| Dried Whole Eggs | 1.22 |
| Codfish Powder | 0.80 |
| Salmon Powder | 1.65 |
| Shrimp Powder | 0.94 |
| Sesame Seed Flour | 1.05 |
| Dry Vitamin D3 100 SD/S | 0.08 |
| Natural Masking Flavor | 9.40 |
| Sweetener | 0.12 |
| Maltodextrin | 45.84 |
| Extra Fine Granulated Sugar | 15.32 |
| Total | 100.00 |

The formulation of an additional exemplary dry powdered mixed allergen composition resulting from the processes described in Examples 1-3 is depicted in TABLE 6. This composition is hereafter referred to as Product E. Product E was based on the formulation of Product A modified with the goal of reducing the sugar content in the mixed allergen composition. 75% of the extra fine granulated sugar was replaced with an agglomerated maltodextrin to improve visual characteristics of the finished product, and sweetener was added to provide sweetness lost due to replacement of sugar by maltodextrin. Blanched almond flour, pecan and pistachio meals were sieved in order to remove large particles from the finished product, therefore visually improving the product.

TABLE 6

| Ingredient | % Dry Blend |
| --- | --- |
| Peanut Flour | 1.13 |
| Soy Protein Isolate | 0.70 |
| Blanched Almond Flour, sieved | 2.80 |
| Cashew Flour | 3.33 |
| Hazelnut Flour | 2.07 |
| Pecan Meal, sieved | 6.67 |
| Pistachio Meal, sieved | 2.86 |
| Walnut Flour | 1.41 |
| Wheat Gluten Powder | 0.79 |
| Oat Protein Powder | 1.11 |
| Milk Protein Isolate | 0.71 |
| Dried Whole Eggs | 1.22 |
| Codfish Powder | 0.80 |
| Salmon Powder | 1.65 |
| Shrimp Powder | 0.83 |
| Sesame Seed Flour | 1.05 |
| Dry Vitamin D3 100 SD/S | 0.08 |
| Natural Masking Flavor | 9.40 |
| Sweetener | 0.12 |
| Maltodextrin | 45.84 |
| Extra Fine Granulated Sugar | 15.43 |
| Total | 100 |

The formulation of an additional exemplary dry powdered mixed allergen composition resulting from the processes described in Examples 1-4 is depicted in TABLE 7. This composition is hereafter referred to as Product F. Product F was based on the formulation of Product C. Product F was modified to remove maltodextrin due to processing challenges. Sweetener was not included in the formulation. Additionally, a 20% vitamin D overage was included based on results described in Example 4, to ensure the final composition after processing contains the targeted vitamin D dose.

TABLE 7

| Ingredient | % Dry Blend |
| --- | --- |
| Peanut Flour | 1.13 |
| Soy Protein Isolate | 0.70 |
| Blanched Almond Flour, sieved | 2.80 |
| Cashew Flour | 3.33 |
| Hazelnut Flour | 2.07 |
| Pecan Meal, sieved | 6.67 |
| Pistachio Meal, sieved | 2.86 |
| Walnut Flour | 1.41 |
| Wheat Gluten Powder | 0.79 |
| Oat Protein Powder | 1.11 |
| Milk Protein Isolate | 0.71 |
| Dried Whole Eggs | 1.22 |
| Codfish Powder | 0.80 |
| Salmon Powder | 1.65 |
| Shrimp Powder | 0.83 |
| Sesame Seed Flour | 1.05 |
| Dry Vitamin D3 100 SD/S | 0.10 |
| Natural Masking Flavor | 9.40 |
| Extra Fine Granulated Sugar | 59.87 |
| Silicon Dioxide Sipernat 50 | 1.50 |
| Total | 100 |

The formulation of an exemplary dry powdered mixed allergen composition resulting from the processes described in Examples 1-2 is depicted in TABLE 8. This composition is hereafter referred to as Product G.

TABLE 8

| Ingredient | % Dry Blend |
| --- | --- |
| Peanut Flour | 1.31 |
| Soy Protein Isolate | 0.74 |
| Blanched Almond Flour | 2.99 |
| Cashew Flour | 3.56 |
| Hazelnut Flour | 2.21 |
| Pecan Meal | 7.12 |
| Pistachio Meal | 3.05 |
| Walnut Flour | 1.51 |
| Wheat Gluten Powder | 0.84 |
| Oat Protein Powder | 1.19 |
| Milk Protein Isolate | 0.75 |
| Dried Whole Eggs | 1.31 |
| Codfish Powder | 0.85 |
| Salmon Powder | 1.76 |
| Shrimp Powder | 1.00 |
| Sesame Seed Flour | 1.12 |
| Dry Vitamin D3 100 SD/S | 0.09 |
| Natural Masking Flavor | 9.46 |
| Extra Fine Granulated Sugar | 57.11 |
| Rice concentrate | 2.03 |
| Total | 100 |

Example 6

This example describes an exemplary microbial reduction treatment for a dry powdered product using a microwave blender.

Product B (as described in Example 5) was subjected to a treatment of 230° F./110° C. for 60 minutes in a WaveMix microwave blender, and the total aerobic organisms were measured before and after treatment. Additionally, Product B was inoculated with a population of an indicator vegetative organism, Enterococcus faecium NRRL B-2354, prior to undergoing treatment in the microwave blender, and the total E. faecium was measured before and after heat treatment for inoculated Product B. E. faecium has been used as a non-pathogenic Salmonella surrogate for thermal lethality studies carried out on dried products because it is relatively heat resistant at lower water activities. In the Examples herein, unless indicated otherwise, the WaveMix microwave blender used was a Model No. SPU-2436 with a 75,000 watt microwave transmitter.

Samples were diluted and spread onto a petri dish of general recovery media to measure colony-forming units per gram of product (CFU/g). For uninoculated Product, the limit of detection for the method was 1 CFU/g for a 1:10 dilution. For inoculated Product, the limit of detection was set to the first serial dilution at which no background microflora growth was observed in the uninoculated samples.

The total aerobic organisms for uninoculated Product B before and after treatment in the WaveMix microwave blender and the log reduction due to treatment are depicted in TABLE 9. The total E. faecium for the inoculated Product B before and after treatment in the WaveMix microwave blender and the log reduction due to treatment are depicted in TABLE 10. Throughout the specification, Avg±SD indicates average±standard deviation. Log reduction was calculated by subtracting the counts from each replicate after treatment from the average count before treatment.

TABLE 9

| | | Total Counts (log CFU/g) | | |
| --- | --- | --- | --- | --- |
| Target Organism | Replicate | Before Treatment | After Treatment | Log Reduction |
| Total aerobic organisms | A | 5.0 | 3.7 | 1.7 |
| | B | 5.5 | 3.9 | 1.5 |
| | C | 5.6 | 3.8 | 1.6 |
| | Avg ± SD | 5.4 ± 0.3 | 3.8 ± 0.1 | 1.6 ± 0.1 |

TABLE 10

| | | Total Counts (log CFU/g) | | |
| --- | --- | --- | --- | --- |
| Target Organism | Replicate | Before Treatment | After Treatment | Log Reduction |
| E. faecium | A | 7.4 | <4.0[1] | >3.5 |
| | B | 7.4 | <4.0[1] | >3.5 |
| | C | 7.5 | <4.0[1] | >3.5 |
| | D | — | <4.0[1] | >3.5 |
| | E | — | <4.0[1] | >3.5 |
| | F | — | <4.0[1] | >3.5 |
| | G | — | <4.0[1] | >3.5 |
| | H | — | <4.0[1] | >3.5 |
| | I | — | <4.0[1] | >3.5 |
| | J | — | <4.0[1] | >3.5 |
| | Avg ± SD | 7.5 ± 0.0 | <4.0[1] | >3.5 |

[1] Below the limit of detection of 4.0 log CFU/g

Uninoculated Product B had a 1-2 log reduction in the background microflora after treatment in the WaveMix microwave blender, while inoculated Product B had a greater than 3.5 log reduction in E. faecium due to treatment in the WaveMix microwave blender.

Product A (as described in Example 5) was subjected to a treatment of 230° F./110° C. for 60 minutes in a WaveMix microwave blender, and the total aerobic organisms were measured before and after treatment. The counts before and after treatment in the WaveMix microwave blender and the log reduction due to treatment are depicted in TABLE 11. Log reduction was calculated by subtracting the counts from each replicate after treatment from the average count before treatment.

TABLE 11

| | | Total Counts (log CFU/g) | | |
| --- | --- | --- | --- | --- |
| Target Organism | Replicate | Before Treatment | After Treatment | Log Reduction |
| Total aerobic organisms | A | 2.7 | 2.9 | No reduction |
| | B | 3.6 | 3.0 | |
| | C | 3.4 | 2.8 | |
| | Avg ± SD | 3.2 ± 0.5 | 2.9 ± 0.1 | |

No reduction in total aerobic organisms was observed in Product A after treatment in the WaveMix microwave blender.

Following treatment, SDS-PAGE testing of Product A was performed as follows. Product A was solubilized in reducing Laemmli buffer to a concentration of 1 mg protein/ml. Samples were mixed, heated at 95° C.-100° C., centrifuged, and loaded onto an SDS-PAGE gel. The gel was run at 100V for 80 to 90 minutes. Following completion, the gel was fixed, stained, destained and imaged. As shown in FIG. 1, SDS-PAGE testing revealed no damage to the protein structure of the Product A components following treatment in the WaveMix microwave blender.

In summary, microbial reduction treatment in a WaveMix microwave blender resulted in a 1-2 log reduction of background microflora for Product B, and a >3.5 log reduction in *E. faecium* when Product B was inoculated with *E. faecium* prior to treatment. No reduction in total microbial content was observed in the background microflora of Product A after treatment in a WaveMix microwave blender. These results suggest that, under certain conditions, microwave blender treatment may substantially reduce population levels of vegetative cells in a dry powdered composition.

Example 7

This example describes an exemplary microbial reduction treatment for a dry powdered product using a microwave blender to treat a wetted product.

Figure 2:
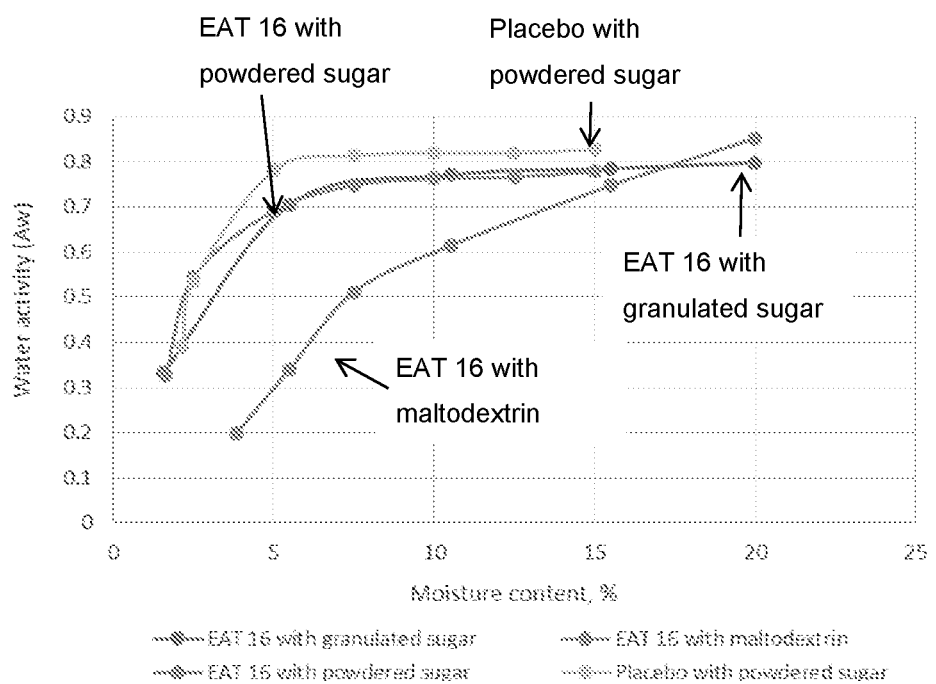
FIG. 2 is a line graph depicting the relationship between moisture and water activity ($a_w$) for the indicated compositions formulated with the indicated bulking agents.

As water activity ($a_w$) may influence the time required for thermal reduction of target microorganisms, the relationship between moisture and water activity was determined for exemplary dry powdered products. Products A and B were prepared as described in Example 5, except with varying bulking agents as described below. Product B was formulated at 15% total fat content using powdered sugar as a bulking agent, and Product A was formulated at 15% total fat content using each of granulated sugar, maltodextrin, and powdered sugar as bulking agents. 700 g of each Product was mixed for five minutes in a five quart KitchenAid mixer bowl using a whisk. Water was added stepwise under agitation for an additional 8 minutes in the KitchenAid mixer, while moisture was measured using a Computrac 1000XL at 135° C. and water activity ($a_w$) measured using a Rotronic HygroLab. The relationship between moisture and water activity for the indicated formulations is depicted in FIG. 2.

Product B formulated with powdered sugar had systematically higher $a_w$ values than Product A, consistently achieving $a_w$>0.8 at moisture levels≥7.5%.

For Product A, granulated sugar and powdered sugar were more effective bulking agents than maltodextrin, as Product A formulated with maltodextrin required more than three times the level of moisture than powdered sugar in order to reach an equivalent $a_w$>0.7. The particle size of sugar used in the experiment did not have a significant effect on the moisture-$a_w$ relationship, as formulations with granulated and powdered sugar bulking agents behaved similarly.

In summary, for the products tested, sugar was the best performing bulking agent by allowing formulation of systems with high water activity at the lowest moisture content values (7.5-10%), which may lead to higher lethality during microwave blender processing. Together, these results suggest that microbial reduction treatment for a mixed allergen composition, e.g., Product A, using a microwave blender may be enhanced by moistening to a 6-9% final moisture content (corresponding to an $a_w$ of 0.65-0.8), and using powdered sugar as a bulking agent.

Based on these results, microbial reduction treatment using a microwave blender was tested on a wetted powdered product. Product G (as described in Example 5) was wetted and subjected to a treatment of 200° F./93° C. for 60 minutes in a WaveMix microwave blender, and then dried in the blender. Total aerobic organisms were measured before water addition and heat treatment, after water addition and before heat treatment, after heat treatment and before drying, and, finally, after drying. Additionally, Product G was inoculated with a population of an indicator vegetative organism, *E. faecium*, prior to wetting and heat treatment, and the total *E. faecium* was measured at each sampling time for the inoculated Product G.

Samples were diluted and spread onto a petri dish of general recovery media to measure colony-forming units per gram of product (CFU/g). For uninoculated Product, the limit of detection for the method was 1 CFU/g for a 1:10 dilution. For inoculated Product, the limit of detection was set to the first serial dilution at which no background microflora growth was observed in the uninoculated samples.

Figure 3:
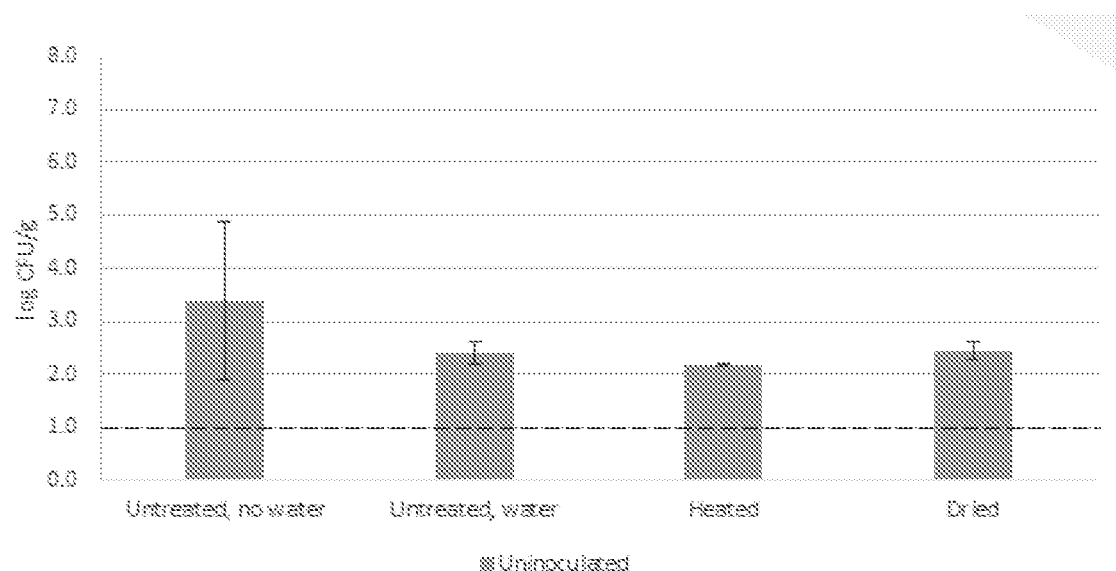
FIG. 3 is a bar graph depicting levels of background microflora in a mixed allergen composition (Product A) at several sampling times during treatment in a WaveMix microwave blender. Vertical lines denote standard deviation (n=3). Dashed line indicates the limit of detection.
Figure 4:
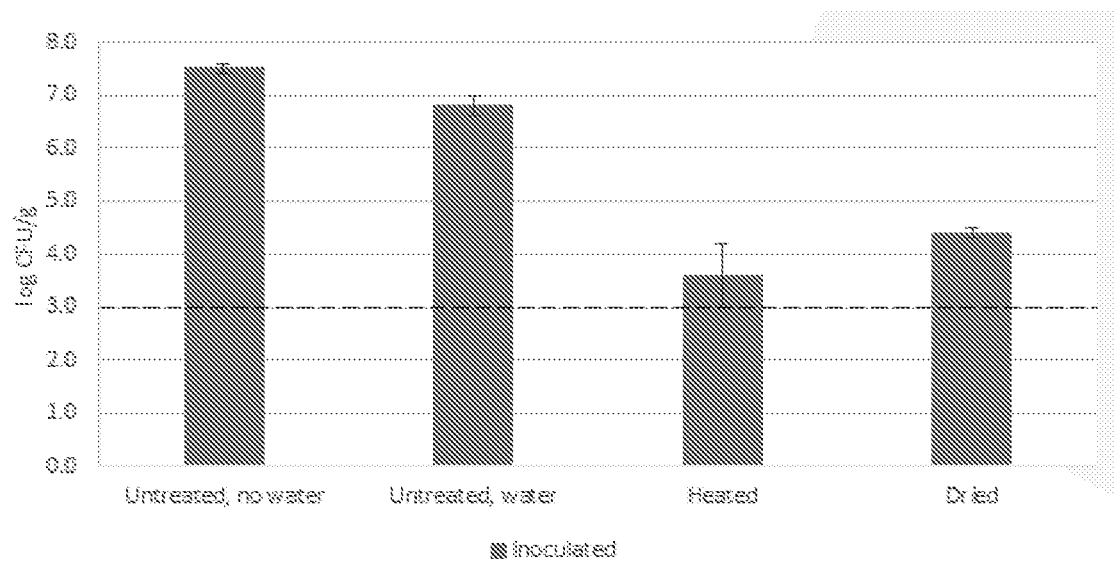
FIG. 4 is a bar graph depicting levels of *Enterococcus faecium* NRRL B-2354 in an artificially-inoculated mixed allergen composition (Product A) at several sampling times during treatment in a WaveMix microwave blender. Vertical lines denote standard deviation (Untreated, no water; Untreated, water; and Heated: n=3; Dried: n=10). Dashed line indicates the limit of detection.

The total aerobic organisms for the uninoculated Product G at the indicated times and the log reduction due to heat treatment are depicted in TABLE 12 and FIG. 3. The total *E. faecium* for the inoculated Product G at the indicated times and the log reduction due to heat treatment are depicted in TABLE 13 and FIG. 4. Log reduction was calculated by subtracting the counts from each replicate after treatment from the average count before treatment.

TABLE 12

| | | Total Counts (log CFU/g) | | | |
|---|---|---|---|---|---|
| Target Organism | Replicate | Untreated, No Water | Untreated, Water | Heated | Dried |
| Total aerobic Organisms | A | 5.1 | 2.1 | 2.2 | 2.6 |
| | B | 2.7 | 2.5 | 2.1 | 2.4 |
| | C | 2.4 | 2.5 | 2.2 | 2.3 |
| | Avg ± SD | 3.4 ± 1.5 | 2.4 ± 0.2 | 2.2 ± 0.0 | 2.4 ± 0.2 |
| | Log Reduction | | No Reduction | No Reduction | No Reduction |

TABLE 13

| | | Total Counts (log CFU/g) | | | |
|---|---|---|---|---|---|
| Target Organism | Replicate | Untreated, No Water | Untreated, Water | Heated | Dried |
| *E. faecium* | A | 7.4 | 6.7 | 3.5 | 4.5 |
| | B | 7.4 | 6.7 | 3.1 | 4.5 |
| | C | 7.7 | 7.1 | 4.2 | 4.3 |
| | D | — | — | — | 4.7 |
| | E | — | — | — | 4.5 |
| | F | — | — | — | 4.5 |
| | G | — | — | — | 4.7 |
| | H | — | — | — | 4.3 |
| | I | — | — | — | 5.2 |
| | J | — | — | — | 4.6 |
| | Avg ± SD | 7.5 ± 0.1 | 6.8 ± 0.2 | 3.6 ± 0.6 | 4.4 ± 0.1 |
| | Log Reduction | | No Reduction | 3.9 ± 0.6 | 2.9 ± 0.3 |

No reduction in the level of background microflora of the uninoculated Product G was observed after treatment in the WaveMix microwave blender, while a 3-4 log reduction in *E. faecium* was observed for the inoculated Product G after treatment in the WaveMix microwave blender.

Figure 5:
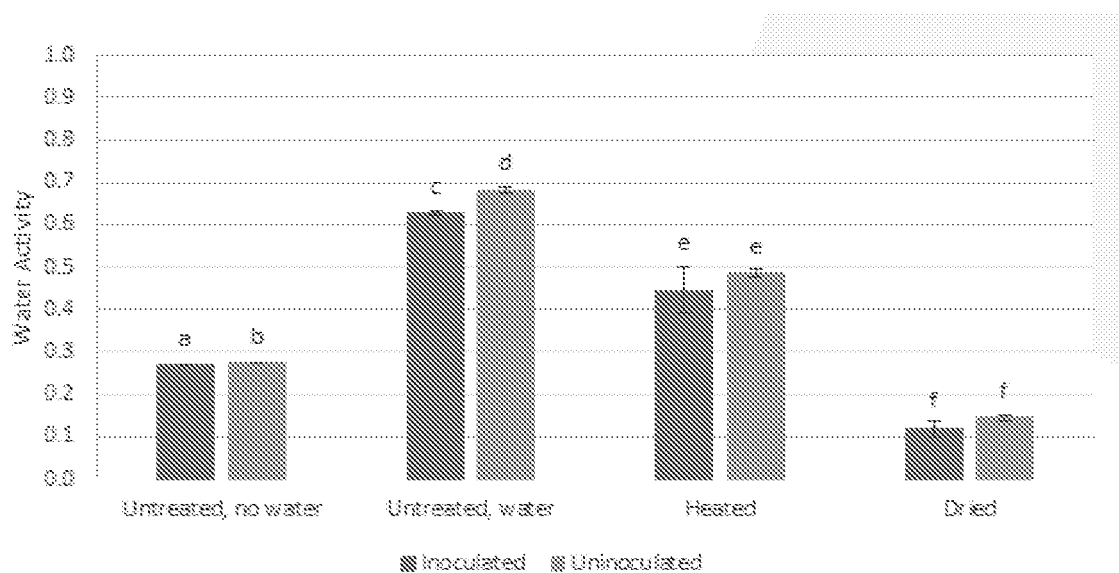
FIG. 5 is a bar graph depicting water activity of a mixed allergen composition (Product A) with and without artificially inoculated *E. faecium* at several sampling times during treatment in the WaveMix microwave blender. Vertical lines indicate standard deviation (n=3). Samples within pairs with the same letter were not statistically different ($\alpha=0.05$).

Water activity and moisture content were also measured throughout the treatment process using a Rotronic HygroLab or AquaLab 4TE and Computrac 1000XL, respectively. Water activity for inoculated and uninoculated Product G at the indicated time points is depicted in FIG. 5, and water activity and moisture content of inoculated and uninoculated Product G at the indicated time points is depicted in TABLE 14.

TABLE 14

| Product | Analysis | Replicate | Untreated, No Water | Untreated, Water | Heated | Dried |
|---|---|---|---|---|---|---|
| Inoculated | Water Activity | A | 0.270 | 0.623 | 0.482 | 0.104 |
| | | B | 0.271 | 0.628 | 0.471 | 0.110 |
| | | C | 0.272 | 0.633 | 0.383 | 0.140 |
| | | Avg ± SD | 0.271 ± 0.001 | 0.628 ± 0.005 | 0.445 ± 0.054 | 0.118 ± 0.019 |
| | Moisture Content | A | 2.73% | 5.47% | 4.11% | 2.32% |
| | | B | 2.86% | 4.94% | 3.23% | 1.89% |
| | | C | 2.85% | 5.26% | 2.85% | 2.46% |
| | | Avg ± SD | 2.81 ± 0.07% | 5.22 ± 0.27% | 3.40 ± 0.65% | 2.22 ± 0.30% |
| Uninoculated | Water Activity | A | 0.274 | 0.687 | 0.474 | 0.136 |
| | | B | 0.272 | 0.675 | 0.494 | 0.146 |
| | | C | 0.275 | 0.684 | 0.487 | 0.151 |
| | | Avg ± SD | 0.274 ± 0.001 | 0.682 ± 0.006 | 0.485 ± 0.010 | 0.144 ± 0.007 |
| | Moisture Content | A | 1.61% | 6.72% | 4.52% | 1.69% |

In summary, microbial reduction treatment in a WaveMix microwave blender resulted in no reduction in background microflora for an exemplary mixed allergen composition; however, treatment resulted in a 3-4 log reduction in *E. faecium* in mixed allergen composition inoculated with *E. faecium* prior to treatment. These results suggest that, under certain conditions, microwave blender treatment may substantially reduce population levels of vegetative cells in a mixed allergen composition.

Example 8

This example describes an exemplary microbial reduction treatment for a dry powdered product using a pressurized heat treatment.

Products A and B are formulated with 12% fat and 6-9% final moisture content with powdered sugar as a bulking agent, and subjected to treatment at 240° F. for 30 minutes at 30 psi and at 200° F. for 60 minutes at atmospheric pressure in a microwave blender. The pressurized treatment allows for higher temperatures without boiling water. Each process is carried out in a closed system environment in order to prevent moisture loss and large shifts in $a_w$ during the heating process.

Example 9

This example describes an exemplary microbial reduction treatment for a dry powdered product using Radio Frequency Interference (RFI).

Radio Frequency (RF) is a long-wave length, non-ionizing form of electrical energy. RF's long-wavelength energy have a superior depth of penetration relative to microwaves, allowing for a rapid, uniform and volumetric heating of a product, simultaneously throughout the entire thickness. Radio frequency can also be carried out both in bulk as well as in packaged material, provided the packaging does not contain a foil component or carbon black markings.

RFI microbial reduction treatment was carried out an exemplary dry powdered mixed allergen composition (Product A as described in Example 5).

Bulk quantities of Product A (approximately 2 pounds) were treated at 250° F., 225° F., 215° F., 205° F., 195° F., and 190° F. in a Macrowave™ radio frequency pasteurization unit.

Microbiological testing was carried out before the RFI treatment, after the lowest heat treatment temperature (190° F.) and after the highest temperature treatment (250° F.). Total coliforms, and total aerobic organisms were determined by spreading diluted samples onto a petri dish of recovery media to measure colony-forming units per gram of product (CFU/g). The results are depicted in TABLE 15. The RFI process reduced the aerobic plate count, with the 190° F. treatment resulting in a 0.7 log reduction, and the 250° F. treatment resulting in a 1.8 log reduction. The RFI process also reduced the total coliforms, with the 190° F. treatment resulting in a 0.5 log reduction, and the 250° F. treatment resulting in a >1.2 log reduction. The 250° F. treatment resulted in a population of coliforms that was beneath the detection threshold.

TABLE 15

| Test | Before Treatment | Low Temperature | High Temperature |
|---|---|---|---|
| Aerobic Plate Count (APC) | 3.8 log CFU/g | 3.1 log CFU/g | 2.0 log CFU/g |
| APC log reduction | — | 0.7 log | 1.8 log |
| Total Coliforms | 2.2 log CFU/g | 1.7 log CFU/g | <1 log CFU/g |

These results suggest that, under certain conditions, RFI treatment may reduce microorganism population in a mixed allergen composition.

Example 10

This example describes an exemplary thermal treatment for a dry powdered product.

Product D (as described in Example 5) was placed into a Kenwood mixer equipped with an induction heating system, and heat treated at 230° F. for 60 minutes under continuous mixing. The Kenwood mixer equipped with an induction heating system mimics the effects of a microwave blender, such as the WaveMix microwave blender, at the bench scale. Although a plastic splash-guard was used as a cover, the system was not closed and as a result moisture could evaporate throughout the treatment.

A comparison of the properties of the heat treated product versus an un-heated control was carried out. The heat treated product was tested as both as a powder, as well as a powder mixed in applesauce. The sweetness, flavor and aroma were not impacted by heat treatment, while the heat treated sample was slightly darker. As a dry powder, the heat treated sample clumped slightly more in the mouth than untreated sample. The heat treated product also clumped slightly upon mixing in applesauce, however, after 2-3 minutes the clumps disappeared and the blend looked homogeneous.

These results suggest that the heat treatment of a mixed allergen composition, e.g., Product D, does not substantially influence taste, color, or clumping of the mixed allergen composition.

Example 11

This example describes an exemplary microbial reduction treatment for a dry powdered product using a microwave blender.

Product C (as described in Example 5) was processed in a pilot plant setting using the following process. All ingredients were weighed and pre-blended in a 10 cubic foot WaveMix microwave blender for 5 minutes. Vitamin D was added and the composition was further blended for 5 minutes to fully disperse the fine powder and attach it to the fatty nut particles in the 16 protein ingredient blend. Sugar and natural masking flavor were added and the composition was further blended for 5 minutes until homogeneous. After preparing the homogeneous blend, heat treatment was carried out in the microwave blender in two phases. In a first heating phase, the microwave power was set at 35 kW and the blender was set at 30 rpm, with the goal of increasing product temperature to 230° F. A typical duration for this stage was 18-21 minutes. In a second holding phase, the product was maintained at 230° F. for 60 minutes under constant agitation at 30 rpm to prevent localized overheating. At the end of the WaveMix process, the product was discharged hot into lined pails and allowed to cool to room temperature for up to 48 hours. After cooling, the product was filled into stick-packs, at a target weight of 5-5.4 g per stick-pack.

Product C (as described in Example 5) was subjected to a treatment of 230° F./110° C. for 60 minutes in a WaveMix microwave blender, and the total aerobic organisms were measured before and after treatment. Additionally, Product C was inoculated with *E. faecium* NRRL B-2354, prior to undergoing treatment in the microwave blender, and the total *E. faecium* was measured before and after heat treatment for inoculated Product C.

Samples were diluted and spread onto a petri dish of general recovery media to measure colony-forming units per gram of product (CFU/g). For uninoculated and inoculated Product C, the limit of detection for the method was 1 CFU/g for a 1:10 dilution.

The total aerobic organisms for uninoculated Product C before and after treatment in the WaveMix microwave blender and the log reduction due to treatment are depicted in TABLE 16. The total *E. faecium* for the inoculated Product C before and after treatment in the WaveMix microwave blender and the log reduction due to treatment are depicted in TABLE 17. Throughout the specification, n/d indicates not determined. Log reduction was calculated by subtracting the counts from each replicate after treatment from the average count before treatment.

TABLE 16

| | | Total Counts (log CFU/g) | | |
|---|---|---|---|---|
| Organism | Replicate | Before Treatment | After Treatment | Log Reduction |
| Background microflora | A | 2.8 | 1.4 | 1.5 |
| | B | 2.4 | 1.8 | 1.1 |
| | C | n/d | 1.6 | 1.3 |
| | D | 3.5 | <1.0[1] | >1.9 |
| | E | 2.9 | <1.0[1] | >1.9 |
| | Avg ± SD | 2.9 ± 0.5 | 1.4 ± 0.4 | 1.5 ± 0.4 |

[1]Below the limit of detection

TABLE 17

| | | Trial 1 | | | Trial 2 | | |
|---|---|---|---|---|---|---|---|
| | | Total Counts (log CFU/g) | | | Total Counts (log CFU/g) | | |
| Organism | Replicate | Before Treatment | After Treatment | Log Reduction | Before Treatment | After Treatment | Log Reduction |
| *E. faecium* | A | 6.7 | <1.0[1] | >5.6 | 6.8 | <1.0[1] | >5.8 |
| | B | 6.7 | <1.0[1] | >5.6 | 6.9 | 1.5 | 5.3 |
| | C | 6.7 | <1.0[1] | >5.6 | 6.7 | <1.0[1] | >5.8 |
| | D | 6.9 | <1.0[1] | >5.6 | 6.7 | 1.2 | 5.6 |
| | E | 6.9 | n/d | >5.6 | 6.8 | 2.5 | 4.3 |
| | F | 6.6 | 1.6 | 5.0 | 6.9 | 1.9 | 4.9 |
| | G | 6.4 | <1.0[1] | >5.6 | 6.9 | 1.2 | 5.6 |
| | H | 6.5 | 1.6 | 5.0 | 6.6 | <1.0[1] | >5.8 |
| | I | 6.4 | 1.2 | 5.4 | 6.6 | <1.0[1] | >5.8 |
| | J | 6.5 | 2.0 | 4.6 | 6.6 | 2.2 | 4.6 |
| | K | — | <1.0[1] | >5.6 | — | <1.0[1] | >5.8 |
| | L | — | <1.0[1] | >5.6 | — | <1.0[1] | >5.8 |
| | M | — | 2.2 | 4.4 | — | <1.0[1] | >5.8 |
| | N | — | 2.1 | 4.5 | — | <1.0[1] | >5.8 |
| | O | — | 1.5 | 5.1 | — | <1.0[1] | >5.8 |
| | P | — | 1.4 | 5.2 | — | <1.0[1] | >5.8 |
| | Q | — | 1.6 | 5.0 | — | 1.4 | 5.4 |

TABLE 17-continued

| | | Trial 1 | | | Trial 2 | | |
| | | Total Counts (log CFU/g) | | | Total Counts (log CFU/g) | | |
| Organism | Replicate | Before Treatment | After Treatment | Log Reduction | Before Treatment | After Treatment | Log Reduction |
|---|---|---|---|---|---|---|---|
| | R | — | 1.2 | 5.4 | — | 1.8 | 5.0 |
| | S | — | <1.0[1] | >5.6 | — | <1.0[1] | >5.8 |
| | T | — | 2.9 | 3.7 | — | <1.0[1] | >5.8 |
| | Avg ± SD | 6.6 ± 0.2 | 1.4 ± 0.5 | 5.2 ± 0.5 | 6.8 ± 0.1 | 1.3 ± 0.5 | 5.5 ± 0.5 |

[1]Below the limit of detection

A 1-2 log reduction in the level of background microflora of the uninoculated Product C was observed after treatment in the WaveMix microwave blender, while a 5 log reduction in *E. faecium* was observed for the inoculated Product C after treatment in the WaveMix microwave blender.

Water activity of Product C was also measured on-site immediately before and after the treatment process and before enumeration in the lab using an AquaLab 4TE. Water activity for inoculated and uninoculated Product C at the indicated time points is depicted in TABLE 18.

TABLE 18

| | | Water Activity | | | | | |
| | | Trial 1 | | Trial 2 | | Trial 3 | |
| Sampling Time | Replicate | Before Treatment | After Treatment | Before Treatment | After Treatment | Before Treatment | After Treatment |
|---|---|---|---|---|---|---|---|
| Utah facility | A | 0.326 | <0.025 | 0.331 | <0.025 | 0.322 | <0.025 |
| Livermore facility | A | 0.327 | 0.083 | 0.348 | 0.042 | 0.343 | 0.052 |
| | B | 0.341 | 0.056 | 0.360 | 0.070 | 0.346 | 0.036 |
| | C | 0.342 | 0.083 | 0.366 | 0.057 | 0.339 | 0.038 |
| | Avg ± SD[1] | 0.337 ± 0.008 | 0.074 ± 0.016 | 0.358 ± 0.009 | 0.056 ± 0.014 | 0.343 ± 0.004 | 0.042 ± 0.009 |

In summary, microbial reduction treatment in a WaveMix microwave blender resulted in a 1-2 log reduction in background microflora for an exemplary mixed allergen composition; however, treatment resulted in a 5-log reduction in *E. faecium* in the mixed allergen composition inoculated with *E. faecium* prior to treatment. These results suggest that, under certain conditions, microwave blender treatment may substantially reduce population levels of vegetative cells in a mixed allergen composition.

Incorporation by Reference

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of making a substantially aerobic organism free mixed allergen composition, comprising:
   providing a mixed allergen composition comprising 6 to 20 allergens and a bulking agent, wherein the mixed allergen composition comprises at least 6% fat content;
   milling the mixed allergen composition in a conical mill to obtain a milled composition with substantially consistent particle size; and
   applying microwaves or radio frequency interference to the milled composition so that the milled composition is heated to at least 190° F. for at least 30 minutes, thereby to obtain the substantially aerobic organism free mixed allergen composition;
   wherein the mixed allergen composition comprises: at least one nut flour, wherein the at least one nut flour is selected from the group consisting of peanut flour, almond flour, walnut flour, cashew flour, hazelnut flour, pecan flour and pistachio flour; at least one fish powder, wherein the at least one fish powder is selected from the group consisting of cod powder and salmon powder; wheat; and powdered hen's egg or egg white.

2. The method of claim 1, wherein the mixed allergen composition comprises at least 12% fat content.

3. The method of claim 1, wherein milling the mixed allergen composition comprises using a rotor speed of about 9000 RPM.

4. The method of claim 1, wherein milling the mixed allergen composition comprises passing the mixed allergen composition through a screen with an opening size of about 0.033 inches.

5. The method of claim 1, wherein milling the mixed allergen composition comprises applying a vacuum suction through the conical mill.

6. The method of claim 1, further comprising wetting the milled composition to a moisture content of about 6% to about 9% prior to applying microwaves or radio frequency interference to the milled mixed allergen composition.

7. The method of claim 6, wherein the milled composition is wetted to a moisture content of about 9% prior to applying microwaves or radio frequency interference to the milled mixed allergen composition.

8. The method of claim 1, further comprising wetting the milled composition to a water activity of about 0.65 to about 0.8 prior to applying microwaves or radio frequency interference to the milled mixed allergen composition.

9. The method of claim 1, wherein the milled composition is heated to at least 200° F. for at least 60 minutes.

10. The method of claim 1, wherein the milled composition is heated to no more than 250° F.

11. The method of claim 1, wherein the milled composition is heated for no more than 360 minutes.

12. The method of claim 1, wherein the milled composition is heated in a microwave blender.

13. The method of claim 1, further comprising pressurizing the milled composition to at least 30 psi for at least 30 minutes.

14. The method of claim 1, wherein the substantially aerobic organism free mixed allergen composition has fewer than about 4.5, about 4, about 3.5, about 3, about 2.5, about 2, or about 1.5 log CFU/g total aerobic organisms.

15. The method of claim 1, wherein the substantially aerobic organism free mixed allergen composition has at least about 0.5, about 1, about 1.5, about 2, about 2.5, about 3, about 3.5, or about 4 log CFU/g fewer total aerobic organisms than the mixed allergen composition.

16. The method of claim 1, wherein the substantially aerobic organism free mixed allergen composition has fewer than about 1 log CFU/g total coliforms.

17. The method of claim 1, wherein the substantially aerobic organism free mixed allergen composition has a substantially similar protein structure as the mixed allergen composition as measured by SDS-PAGE.

18. The method of claim 1, wherein the substantially aerobic organism free mixed allergen composition has a substantially similar allergen effect as the mixed allergen composition as measured by immune response in a patient.

19. The method of claim 1, wherein the bulking agent comprises a sugar.

20. The method of claim 1, wherein the mixed allergen composition further comprises at least one additional allergen component selected from the group consisting of oat flour, sesame seed flour, and shrimp flour.

21. The method of claim 1, wherein the mixed allergen composition further comprises soy.

22. The method of claim 1, wherein the mixed allergen composition comprises:

30 mg by protein weight shrimp powder;

30 mg by protein weight almond powder;

30 mg by protein weight wheat;

30 mg by protein weight cod powder; and 30 mg by protein weight powdered hen's egg.

23. A method of making a substantially aerobic organism free mixed allergen composition, comprising:

providing a mixed allergen composition comprising 6 to 20 allergens and a bulking agent, wherein the mixed allergen composition comprises at least 6% fat content;

milling the mixed allergen composition in a conical mill to obtain a milled composition with substantially consistent particle size, wherein milling the mixed allergen composition comprises applying a vacuum suction through the conical mill; and applying microwaves or radio frequency interference to the milled composition so that the milled composition is heated to at least 190° F. for at least 30 minutes, thereby to obtain the substantially aerobic organism free mixed allergen composition.

24. The method of claim 23, wherein the substantially aerobic organism free mixed allergen composition has fewer than about 4.5, about 4, about 3.5, about 3, about 2.5, about 2, or about 1.5 log CFU/g total aerobic organisms.

25. The method of claim 23, wherein the substantially aerobic organism free mixed allergen composition has at least about 0.5, about 1, about 1.5, about 2, about 2.5, about 3, about 3.5, or about 4 log CFU/g fewer total aerobic organisms than the mixed allergen composition.

26. The method of claim 23, wherein the substantially aerobic organism free mixed allergen composition has fewer than about 1 log CFU/g total coliforms.

27. The method of claim 23, wherein the substantially aerobic organism free mixed allergen composition has a substantially similar protein structure as the mixed allergen composition as measured by SDS-PAGE.

28. The method of claim 23, wherein the substantially aerobic organism free mixed allergen composition has a substantially similar allergen effect as the mixed allergen composition as measured by immune response in a patient.

* * * * *